(12) United States Patent
Jones

(10) Patent No.: US 7,119,903 B1
(45) Date of Patent: Oct. 10, 2006

(54) METHOD AND SYSTEM FOR MEASURING DIFFERENTIAL SCATTERING OF LIGHT OFF OF SAMPLE SURFACES

(75) Inventor: Brian B. Jones, Sunnyvale, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 326 days.

(21) Appl. No.: 10/692,704

(22) Filed: Oct. 24, 2003

Related U.S. Application Data

(60) Provisional application No. 60/429,181, filed on Nov. 25, 2002.

(51) Int. Cl.
*G01N 21/47* (2006.01)

(52) U.S. Cl. ..................................... 356/446
(58) Field of Classification Search ......... 356/445–448
See application file for complete search history.

(56) References Cited

U.S. PATENT DOCUMENTS 6,034,776 A * 3/2000 Germer et al. .............. 356/369

\* cited by examiner

*Primary Examiner*—Layla G. Lauchman
*Assistant Examiner*—Amanda Merlino
(74) *Attorney, Agent, or Firm*—McDermott Will & Emery LLP

(57) ABSTRACT

A method is provided for estimating scattering and includes providing a distribution expression that includes first, second, and third integrals over a source solid angle, a sample area, and detector solid angle respectively, and an integrand that includes a differential-scattering profile; approximating the first and second integrals to be the second integral, wherein the source electromagnetic radiation is approximated to be collimated; approximating the second and third integral to be the third integral, wherein a detector for detecting the electromagnetic radiation scattered from the surface is approximated to be a point detector; transforming the coordinates of the third integral over detector solid angle to be a fourth integral over a single dimension in cosine space, wherein the surface is approximated to be shift invariant; differentiating the fourth integral with respect to the single dimension to generate the differential-scattering profile; and generating an optical system design based on the differential-scattering profile.

32 Claims, 11 Drawing Sheets

METHOD AND SYSTEM FOR MEASURING DIFFERENTIAL SCATTERING OF LIGHT OFF OF SAMPLE SURFACES

CROSS-REFERENCES TO RELATED APPLICATIONS

This application claims priority to U.S. Provisional Patent Application 60/429,181, filed Nov. 25, 2002, titled METHOD AND SYSTEM FOR MEASURING DIFFERENTIAL SCATTERING OF LIGHT OFF OF SAMPLE SURFACES, and is incorporated by reference herein for all purposes.

BACKGROUND OF THE INVENTION

The present invention relates generally to an optical system, and more particularly related to a method and system for predicting the directions and intensities at which light scatters from a surface, such that a scattering prediction includes a substantially continuous solution over a set of scattering angles that includes specular and non-specular scattering angles, wherein the scattering prediction may be used to generate improved optical systems and improved scattering simulations.

Scattering of stray light in optical devices, such as lenses, telescopes and the like, is a phenomenon that optical designers generally prefer to reduce. Stray light scattering generally refers to the scatter of stray light in an optical system from a surface, such as body portions of lens or telescope. Stray light in an optical system includes light that has separated from an optical signal and often travels along undesired paths. For example, stray light in the lens of a camera can cause photographic images to be formed that have aberrant light features that were not present in a photographed scene.

Designers of optical system typically aim to reduce stray light generation and, once generated, to lower its degrading effect. To lower the degrading effects of stray light scatter, optical designers strive to generate relatively accurate predictive models of light scattering from surfaces. In generating relatively accurate models of light scattering from surfaces, stray light scattering may be better understood and compensated for in the design of optical systems. Models for stray light scattering can be incorporated in optical design programs that show the deleterious effects of stray light scattering as predicted by the models. Stray light scattering estimations calculated prior to building an optical system, can be used to improve final designs to build improved optical systems.

While understanding stray light scattering in optical systems may be used to improve optical systems through improved optical system designs, models for stray light scattering can also be used in light simulation systems, such as in a computer graphics program (e.g., video games, and movie animations). Relatively accurate prediction of stray light scattering from a surface can be used in a computer graphic to simulate scattering from a surface that is substantially realistic.

Predictive light scattering has historically been a diagnostic tool in the field of surface roughness measurements. It was realized relatively early in the study of scattering that the distribution of scattering from a surface can be related to the power spectral density of variations in surface heights of the surface. Generating relatively accurate models of power spectral density as related to surface height variation has provided for the extraction of surface height information from measured power spectral densities to characterize surfaces. See, for example, the studies of James Elmer Harvey reported in Light-Scattering Characteristics of Optical Surfaces, dissertation submitted to the Faculty of the Committee on Optical Sciences, The University of Arizona, 1976, herein Harvey '76. While predictive models of scattering have been used with some success in predicting scattering from surfaces and thus providing extraction of surface height information (e.g., degree that a surface resembles a diffraction grating pattern) from a surface, predictive models of scattering have generally provided non-continuous solutions, for example, between specular and non-specular regions of scatter. Scattering regions for which known models of scattering break down are often compensated for with empirical scattering data or intuitively estimated. However, compensating empirically or intuitively for the shortcomings of known models of scattering tends to be relatively time consuming and often costly as technicians and/or engineers often fill in manually, regions for which known scattering models break down.

Measurement techniques and models for stray light scattering have historically been non-differential techniques. Non-differential techniques and models yield results that often include scattering information of a particular lab setup as well as scattering information of a sample. Separation of lab setup information from sample information in both measurement techniques and models of stray light scattering is often intuitively or empirically carried out. Addition steps of intuitive and/or empirical processing for isolating scattering information from lab setup information is often costly, time consuming, and may produce less than optimal results.

Accordingly, what is needed are improved methods and systems for predicting scattering of stray light from surfaces and more specifically what is needed are models of stray light scattering that generate continuous scattering solutions over a set of scattering angles that includes specular and non-specular scattering angles, wherein the scattering predictions may be used in computer design and computer simulations to generate improved optical systems and improved scattering simulations.

BRIEF SUMMARY OF THE INVENTION

The present invention provides an optical system, and more particularly provides a method and system for predicting the directions and intensities at which light scatters from a surface, such that a scattering prediction includes a substantially continuous solution over a set of scattering angles that includes specular and non-specular scattering angles, wherein the scattering prediction may be used to generate improved optical systems and improved scattering simulations.

According to one embodiment, a computerized method is provided for estimating scattering of electromagnetic radiation from a surface. The method includes providing a distribution expression that includes a first integral over a source solid angle, a second integral over a sample area, a third integral over detector solid angle, and an integrand that includes a differential-scattering profile; approximating the first and second integrals to be the second integral, wherein the source electromagnetic radiation is approximated to be collimated; approximating the second and third integral to be the third integral, wherein a detector for detecting the electromagnetic radiation scattered from the surface is approximated to be a point detector; transforming the coordinates of the third integral over detector solid angle to first and second dimensions in cosine space to form a fourth integral, wherein the surface is approximated to be shift invariant; integrating over the first dimension of the fourth integral; differentiating the fourth integral with respect to the second dimension to generate the differential-scattering profile; and generating an optical system design based on the differential-scattering profile. According to a specific embodiment, the distribution expression includes a bidirectional reflectance distribution function (BRDF). According to another specific embodiment, the differential-scattering profile is a continuous solution representing an algebraic model of specular scattering and non-specular scattering of the electromagnetic radiation from the surface. According to another specific embodiment, the differentiating step includes deconvolving the fourth integral. According to another specific embodiment, the step of approximating the first and second integrals to be the second integral includes approximating a one-to-one correspondence between a differential element of the source electromagnetic radiation and a differential surface area of the surface. According to another specific embodiment, the step of approximating the second and third integral to be the third integral includes approximating that electromagnetic scattered from a differential surface area sources is incident on the point detector.

According to another embodiment, a computerized method is provided for estimating scattering of electromagnetic radiation from a surface. The method includes providing a distribution expression that includes a first integral over a source solid angle, a second integral over a sample area, a third integral over detector solid angle, and an integrand that includes a differential-scattering profile; approximating the first and second integrals to be the second integral, wherein source electromagnetic radiation is approximated to be collimated; approximating third integral to be one based on detecting the electromagnetic radiation scattered from the surface at an imaging detector; transforming the coordinates of the second integral over the sample area to first and second dimensions in cosine space to form a fourth integral, wherein the surface is approximated to be shift invariant; integrating over the first dimension of the fourth integral; differentiating the fourth integral with respect to the second dimension to generate the differential-scattering profile; and generating an optical system design based on the differential-scattering profile.

According to another embodiment, an optical system is provided and includes a collimated beam of electromagnetic radiation configured to illuminate a sample surface, the sample surface being shift invariant; an imaging detector configured to collect electromagnetic radiation scattered from the sample surface, the imaging detector configured to collect the scattered electromagnetic radiation at a plurality of scattering angels to generate a scattering profile; and a computer device configured to generate an estimated-differential-scattering profile and compare the scattering profile and the estimated-differential-scattering profile to generate an optical system design, wherein the estimated-differential-scattering profile is a continuous solution of an differential model of spectral scattering and non-spectral scattering derived from a deconvolution of a bidirectional reflectance distribution function (BRDF). According to a specific embodiment, an expression for the BRDF includes a first integral over a source solid angle, a second integral over the sample surface, a third integral over detector solid angle, and an integrand that includes the estimated-differential-scattering profile; the first and second integrals are approximated to be the second integral based on the source electromagnetic radiation being in the form of the collimated beam; the third integral is approximated to be one based on the detector being an imaging detector; the second integral is are transformed from an integral over detector solid angle to a fourth integral over first and second dimensions in cosine space based on the sample surface being shift invariant; and the fourth integral is integrated with respect to the first dimension and deconvolved with respect to the second dimension to generate the estimated differential-scattering profile.

Numerous benefits may be achieved using the present invention over conventional techniques. For example, the invention provides for estimating differential-scattering profiles from surfaces, wherein the differential-scattering profiles are continuous solutions between specular and non-specular regions of scattered electromagnetic radiation scattered from a surface. Continuous differential-scattering profiles may be used to build improved optical systems, such as lenses and telescopes, that have reduced scattering or for which scattered radiation can be compensated for to lower the deleterious affects of the scattered radiation. Continuous differential-scattering profiles may also be used to build improved computer graphics programs (e.g., computer game graphics) to more accurately represent electromagnetic radiation reflected form graphical computer objects. Depending on the specific embodiment, there can be one or more of these benefits. These and other benefits can be found throughout the present specification and more particularly below.

A further understanding of embodiments of the invention will be understood by reference to the following detailed descriptions and claims, and to the appended drawings.

DESCRIPTION OF SPECIFIC EMBODIMENTS

The present invention provides an optical system, and more particularly provides a method and system for predicting the directions and intensities at which light scatters from a surface, such that a scattering prediction includes a substantially continuous solution over a set of scattering angles that includes specular and non-specular scattering angles, wherein the scattering prediction may be used to generate improved optical systems and improved scattering simulations.

Figure 1:
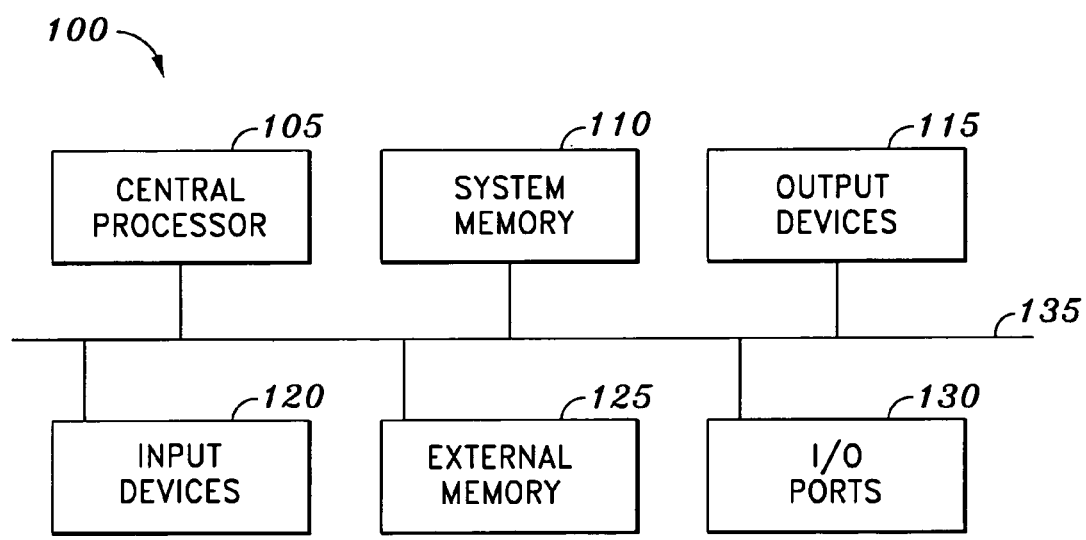
FIG. 1 is a block diagram of a computer system in which embodiments of the present invention may be implemented.

FIG. 1 is a block diagram of a computer system 100 in which embodiments of the present invention may be implemented. A specific embodiment of the invention is implemented on a computer system 100 having a processor 105, a system memory 110, output devices 115, input devices 120, a disk memory 125, I/O (input output) ports 130 and an interconnecting device 135. Processor 105 may be implemented in a variety of formats, such as, but not limited to, a microprocessor, a microcontroller, a microcomputer, embedded logic or other processor types. Processor 105 may be a microprocessor manufactured, for example, by Intel Corporation, Motorola, Inc., or Advanced Micro Devices, Inc. System memory 110 may include EPROMs, EEPROMS, flash memory, SRAMs, DRAMs, cache memory and the like. Output devices 115 may include a variety of device types, such as CRTs, liquid-crystal display panels, printers, computer networks, an audio playback device and the like. Input devices 120 may include a variety of device types, such as a microphone, a keyboard, a computer network and the like. I/O ports 130 may include serial and parallel ports of various designs, such as skuzzy ports, universal serial buses (USB) and the like. It should be understood that computer 100 may be local computer system, such as a personal computer, a distributed system with various modules located at a variety of locations connected by interconnect device 135 that may be a network, such as a WAN, a LAN, the Internet, or a PC system bus. A computer software program stored on system memory 110 and/or disk memory 125 is configured to generate machine code instructions that implement embodiments of the present invention. While various aspects of the invention may be implemented in software, aspects of the invention may be implemented in hardware, firmware, control logic, or a combination of the foregoing.

Figure 2:
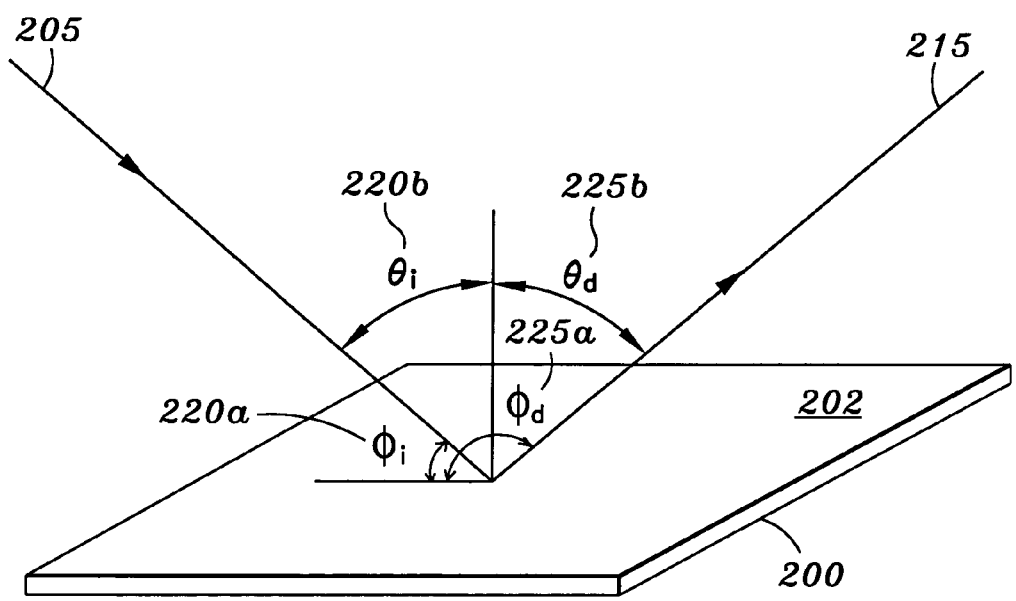
FIG. 2 shows a sample having a surface from which incident electromagnetic radiation may be scattered.

FIG. 2 shows a sample 200 having a surface 202 from which incident electromagnetic radiation 205 is scattered. Scattered electromagnetic radiation is identified by reference numeral 215. Incident electromagnetic radiation 215 is shown to be incident on surface 202 at incident angels $\phi_i$ and $\theta_i$ (identified by reference numerals 220a and 220b, respectively) and scattered into scattering angles $\phi_d$ and $\theta_d$ (identified by reference numerals 225a and 225b, respectively). Distribution of electromagnetic radiation into angles $\phi_d$ and $\theta_d$ may be described by the bidirectional reflectance distribution function (BRDF). The BRDF is a generalized formula for modeling scattering, such as stray light scattering, of light from a source scattered from a surface. The BRDF may be written as follows:

$$BRDF = \frac{1}{P_i}\frac{1}{\Omega_i}\int_{\Omega i}\int_{Area}\int_{\Omega d}\frac{d^2 P_i}{d\Omega_i dA}\frac{dp_d(\Omega_i, \Omega_d, A)}{d\Omega_d} d\Omega_i dA d\Omega_d.$$

In the BRDF, $\Omega_i$ is the solid angle of incident electromagnetic radiation 205 incident on surface 202. $P_i$ is incident electromagnetic radiation 205 and may represent incident power, incident intensity or the like. $\Omega_d$ is the solid angle of scattered electromagnetic radiation 215 scattered from surface 202. $P_d$ is the scattered electromagnetic radiation 215 and may represent scattered power, scattered intensity or the like. A is the area on which incident electromagnetic radiation 205 strikes surface 202.

$$\frac{dp_d(\Omega_i, \Omega_d, A)}{d\Omega_d}$$

is the differential-scattering profile (DSP) of scattered electromagnetic radiation 215. The BRDF is normalized by the factors $$\frac{1}{P_i} \text{ and } \frac{1}{\Omega i}.$$

Each of the integrals shown in the BRDF is a combination of two integrals. The integral over the differential solid angle $d\Omega_i$ represents integrals over the incident angles $\phi_i$ and $\theta_i$, having differentials $d\phi_i$ and $d\theta_1$, respectively. The integral over the differential solid angle $d\Omega_d$ represents integrals over the incident angles $\phi_d$ and $\theta_d$, having differentials $d\phi_d$ and $d\theta_d$, respectively, and the integral over the differential area dA represents integrals over surface coordinates, such as x and y having differentials dx and dy, respectively. While dA is described as being a differential of x and y, which may be linear coordinates, dA may be a differential of polar coordinates or the like.

According to one embodiment, the BRDF is simplified and deconvolved such that the differential-scattering profile $$\frac{dp_d(\Omega_i, \Omega_d, A)}{d\Omega_d}$$

of scattered electromagnetic radiation 215 is solved for. Deconvolution may be roughly thought of as inverting the integrals to extract the integrand (i.e., $$\left(i.e., \frac{dp_d(\Omega_i, \Omega_d, A)}{d\Omega_d}\right).$$

Simplifications of the BRDF include differential simplifications, which yield a differential-scattering profile that is a continuous solution/model for scattered electromagnetic radiation 215 from specular regions into non-specular regions. Two exemplary methods for simplifying and deconvolving the BRDF are explained in detail below. Each exemplary method will be described in combination with respective high-level flow charts outlining steps included in the exemplary methods.

Figure 3:
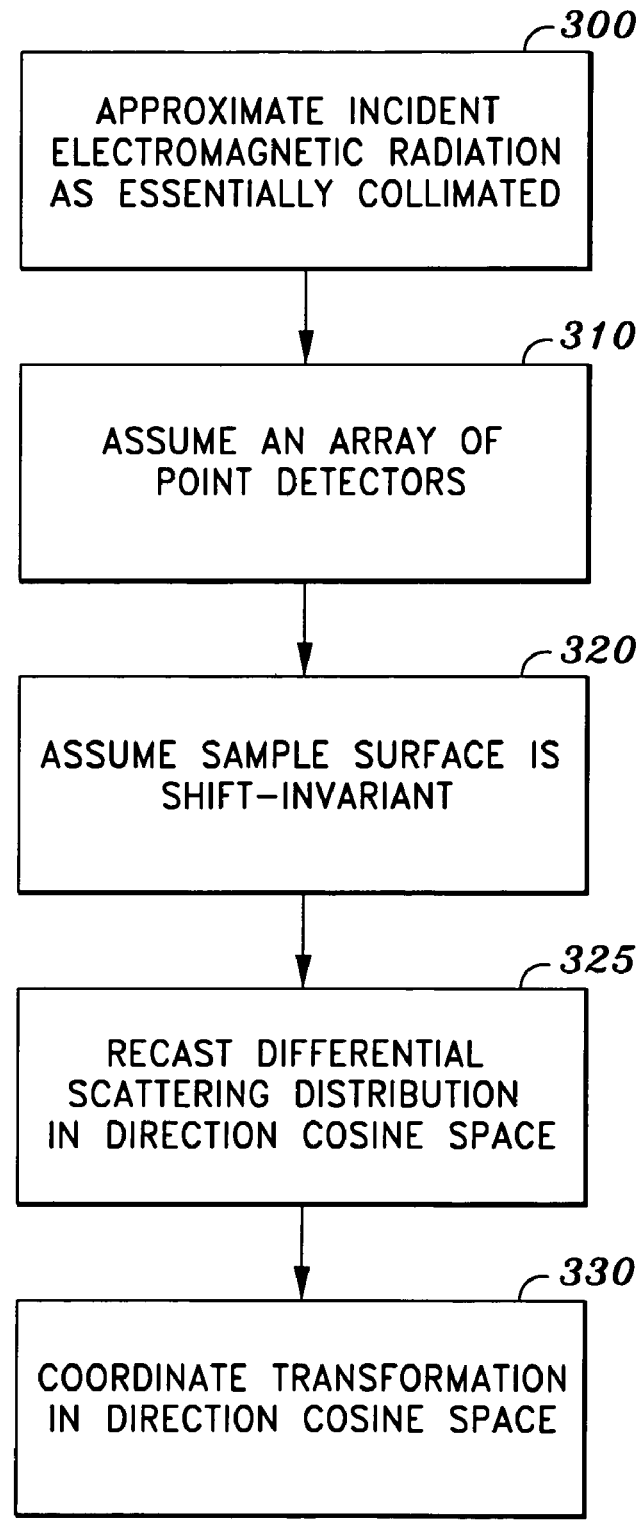
FIG. 3 is a high-level flow chart having steps for deconvolving the bidirectional reflectance distribution function (BRDF) according to an embodiment of the present invention.

FIG. 3 is a high-level flow chart having steps for simplifying and deconvolving the BRDF according to an embodiment of the present invention. It should be realized that the steps shown in FIG. 3 are not limiting on the invention as recited in the claims. Other techniques having fewer, substitute, and/or additional steps are within the purview of the invention and will be readily apparent to those of skill in the art. At 300, incident electromagnetic radiation is approximated as being essentially collimated. From a physical optics point of view, this means that the rays of incident electromagnetic radiation 205 are essentially parallel. In view of this approximation, rays of incident electromagnetic radiation emanating from a unique differential solid angle $d\Omega_i$ are incident on a corresponding unique differential surface area dA.

Figure 4:
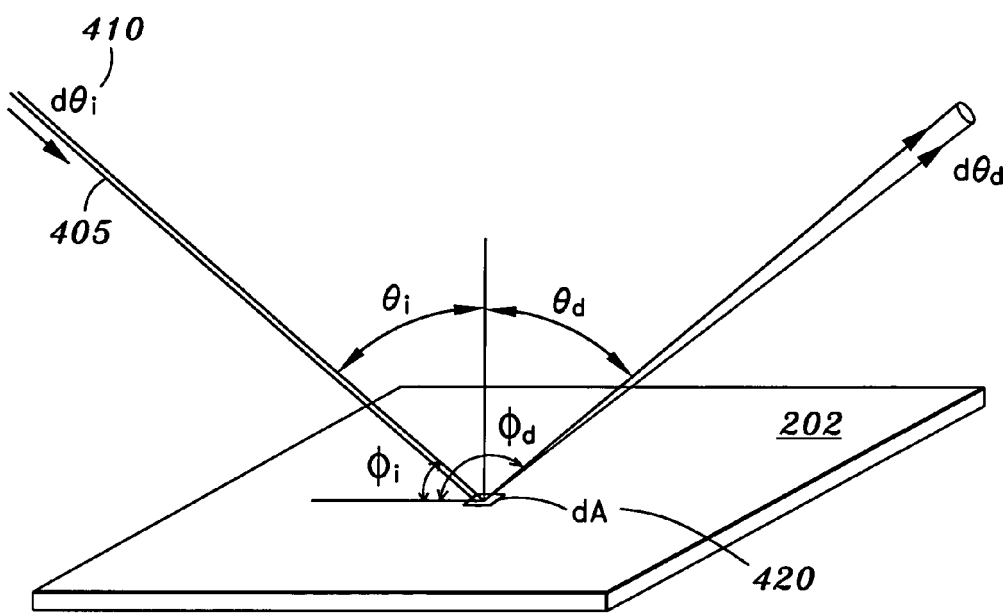
FIG. 4 shows electromagnetic radiation emanating form a unique differential solid angle and traveling essentially parallel onto a differential element of the surface.

FIG. 4 shows rays 405 emanating from a unique differential solid angle 410 and traveling essentially parallel and incident on a differential element 420 of surface 202. As there is an essentially one-to-one relationship between unique differential source solid angles $d\Omega_i$ and unique differential surface area dA, the contribution to the BRDF from these differentials is a delta function for each unique differential source solid angles $d\Omega_i$ and corresponding unique differential surface area dA. Therefore, the integral over either the source solid angle or the integral over the surface area of the sample can be replaced with one. In the embodiment presently described, the integral over the source solid angle will be set to one. An embodiment in which the integral over the surface area is set to one will be described below. Setting the integral over the differential solid angle $d\Omega_i$ to one may be viewed as combining the integral of the differential solid angle $d\Omega_i$ and the differential surface area dA due to the interdependency of these differentials from the collimation assumption.

As the integral over the differential solid angle $d\Omega_i$ has been set to one, the expression for the BRDF has been reduced to a four dimensional integral that may be written as:

$$BRDF = \frac{1}{P_i}\frac{1}{\Omega_i}\int_{Area}\int_{\Omega d}\frac{dP_i}{dA}\frac{dp_d(\Omega_i, \Omega_d, A)}{d\Omega_d}dA d\Omega_d.$$

At 310, a point detector is assumed to collect scattered electromagnetic radiation 215 scattered from surface 202. Detectors that may approximate point detectors include, for example, photomultiplier tubes, silicon diode detectors or the like. In view of this approximation, the integral over the differential scattering solid angle $d\Omega_d$ becomes a delta function and may be set to one. As the integral of the differential scattering solid angle $d\Omega_d$ is set to one, the BRDF may be rewritten as:

$$BRDF = \frac{1}{P_i}\frac{1}{\Omega_i}\int_{Area}\frac{dP_i}{dA}\frac{dp_d(\Omega_i, \Omega_d, A)}{d\Omega_d}dA.$$

At 320, sample surface 202 is assumed to be shift-invariant, isotropic, and homogenous. Shift-invariance implies that the shape of the differential-scattering profile does not changes in direction-cosine space with the angle of incidence and implies that $$\frac{dp_d(\Omega_i, \Omega_d, A)}{d\Omega_d}$$

depends on $|\beta-\beta_0|$. $\beta$ is a coordinate in direction-cosine space and $\beta_0$ is a constant. Shift-invariance further implies that $$\frac{dp_d(\Omega_i, \Omega_d, A)}{d\Omega_d}$$

does not depend of surface position, surface orientation, or absolute scattering angle. $|\beta-\beta_0|$ relates to scattering solid angle $\Omega_d$ via the relationship, $|\beta-\beta_0|=(\sin^2\theta_i+\sin^2\theta_d-2\sin\theta_i\sin\theta_d\cos\Delta\phi_d)^{1/2}$ (this relationship is discussed in further detail below).

Figure 5:
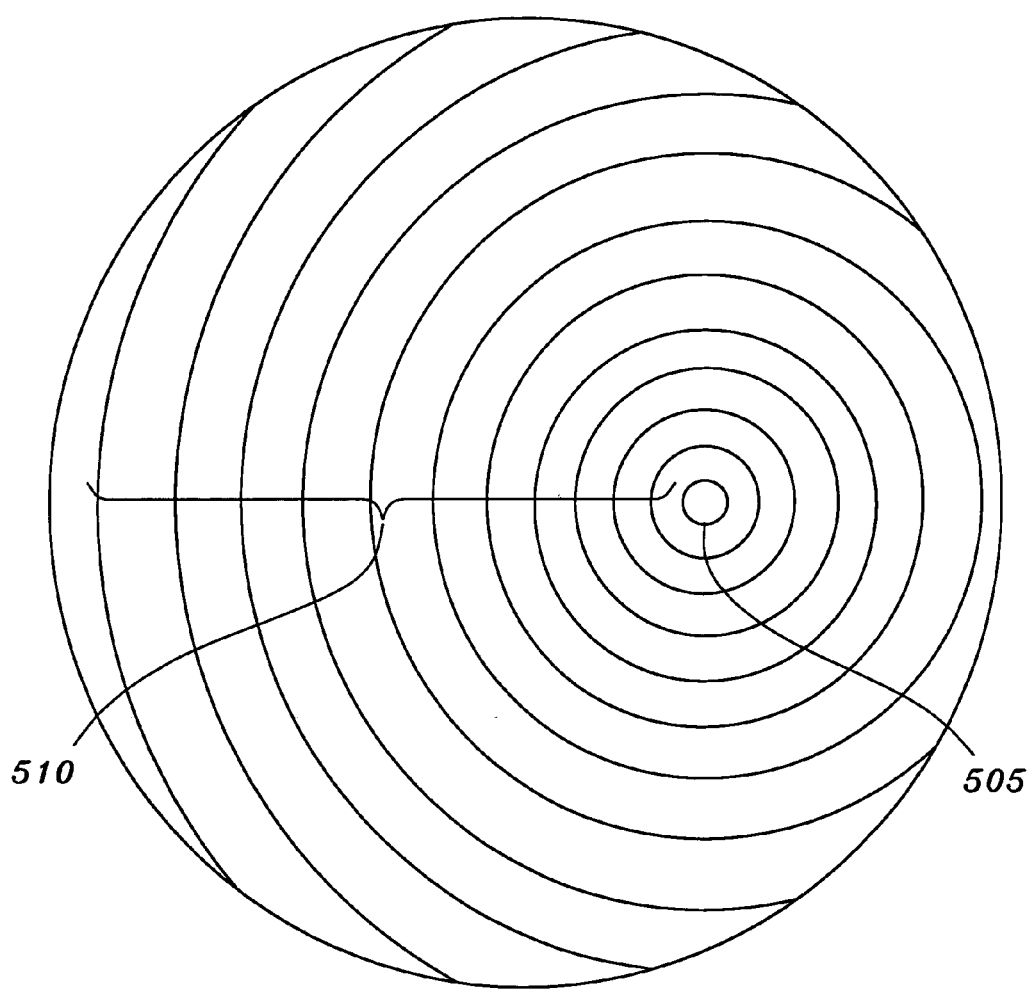
FIG. 5 shows a scattering distribution in direction-cosine space for a shift-invariant, isotropic, and homogenous surface.

In direction-cosine space, scattering intensities are equal on symmetric curves around the specular reflection. FIG. 5 shows a scattering distribution in direction-cosine space for a shift-invariant, isotropic, and homogenous surface. Central circle 505 represents the specular reflection and each symmetric curve 510 around central circle 505 has an equal scattering intensity along its curve. At 330, the differential scattering distribution may be rewritten in direction cosines space as $$BRDF = \frac{1}{P_i}\frac{1}{\Omega_i}\int_{Area}\frac{dP_i}{dA}\frac{dp_d(|\beta-\beta_0|)}{d\Omega_d}dA.$$

In direction cosine space along radii that perpendicularly intersect central circle 505 and symmetric curves 510, the intensity of the scattered electromagnetic radiation changes as a function of radius r. At 340, a coordinate transformation is made in direction cosine space. The coordinate system includes one coordinate $\phi$ lying along the curves of constant $|\beta-\beta_0|$ and the other coordinate r is perpendicular to symmetric curves 505 and 510 (i.e., in the $|\beta-\beta_0|$ direction). The variable r is a function of $|\beta-\beta_0|$.

The integral along curves of constant $|\beta-\beta_0|$ are the path length of the curves (i.e., constants). A single integral is left over $|\beta-\beta_0|$ that is simply an integral along the constant curves of $|\beta-\beta_0|$. That is, dA may be written as $d|\beta-\beta_o|d\alpha$, which yields the equation $$BRDF = \frac{1}{P_i}\frac{1}{\Omega_i}\int_{Area}\frac{dP_i}{dA}\frac{dp_d(|\beta-\beta_0|)}{d\Omega_d}d|\beta-\beta_o|d\alpha.$$

The integral along $d|\beta-\beta_o|$ are path lengths of constant curves of $|\beta-\beta_o|$. Both sides of the BRDF are integrated to yield an expression for the differential-scattering profile:

$$\frac{dp}{d\Omega} = \frac{1}{I_s l(r)r}\frac{dBDRF}{dr},$$

wherein r is a coordinate that is a function of $|\beta-\beta_0|$ and l(r) is the range of the perpendicular coordinate.

The following discussion describes a formalization for r and a formalization of a coordinate system. To build a coordinate system based on contours of constant $|\beta-\beta_0|$, a determination is made as to how $|\beta-\beta_0|$ maps to surface 202. According to the formalization, a detector configured to detect scattered electromagnetic radiation is located at a fixed point and reflection points for the scattered electromagnetic radiation is moved across the surface in such a way as to maintain constant $|\beta-\beta_0|$. For a fixed reflection point, reflection angles corresponding to constant $|\beta-\beta_0|$ trace out a set of observers, such that the projected positions are a circle on the surface. That is, the locus of points of constant distance to the center is a circle. Since the rules of vector addition do not depend on where vectors are, a locus of reflection points for $|\beta-\beta_0|$ will also be a circle (as viewed by a fixed observer).

Figure 6:
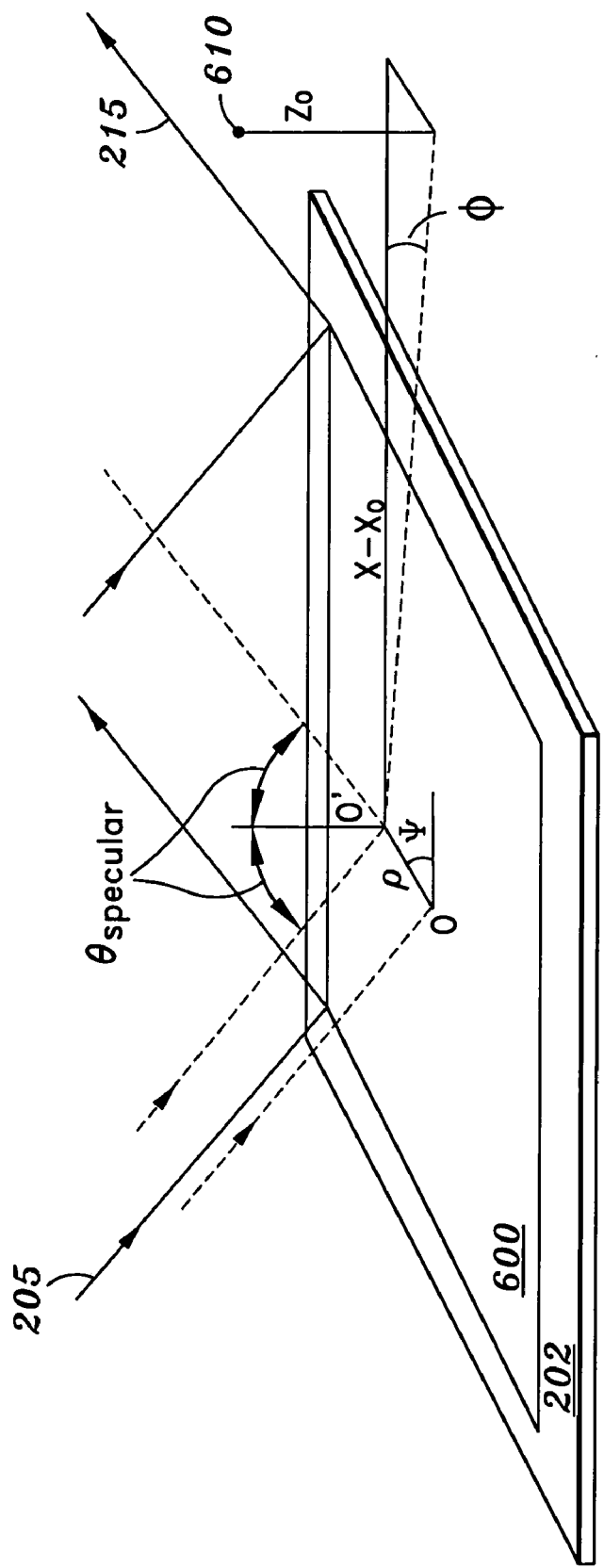
FIG. 6 shows the reflection coordinate system (r, $\phi$) for scattered electromagnetic radiation scattered from an illumination spot that is illuminated by incoming electromagnetic radiation.

The coordinate system, therefore, consists of circles and a radial coordinate, wherein the radial coordinate is a function only of $|\beta-\beta_0|$. The circles are not necessarily equally spaced. The center O' of the reflection coordinate system is a point with $|\beta-\beta_0|=0$. The point $|\beta-\beta_0|=0$ is the specular reflection point. A coordinate system having a center O' that is the specular reflection point is referred to herein as the reflection coordinate system and is described with the coordinates (r, $\phi$). FIG. 6 shows the reflection coordinate system (r, $\phi$) for scattered electromagnetic radiation 215 scattered from an illumination spot 600 that is illuminated by incoming electromagnetic radiation 205.

Another natural choice for a coordinate system is the center O of illumination spot 600. For convenience illumination spot 600 is shown to be circular, however, this is not necessary. The illumination spot may be square or other convenient shape. See, for example, the discussion found in *Light-Scattering Characteristics of Optical Surfaces*, of James Elmer Harvey, dissertation submitted to the Faculty of the Committee on Optical Sciences, The University of Arizona, 1976, herein Harvey '76. The coordinate system centered at the illumination spot is referred to that the spot coordinate system. Coordinates for the spot coordinate system are written in term of ($\rho$, $\psi$). The origin O' of the reflection coordinate system written in terms of spot coordinates may be written as ($\rho_{spec}$, $\psi_{spec}$).

For convenience, the position of a detector 610 (see FIG. 6) is written in Cartesian coordinates as ($x_0$, $y_0$, $z_0$). Writing the location of the detector in terms of Cartesian coordinates facilitates and simplifies transformations between the reflection and spot coordinate systems. The x-axis is set parallel to the line connecting the specular point with the detector. The position of the detector is the only point out of the z=0 plane (plane of the sample) that is taken into consideration in developing expressions for r and for the reflection and spot coordinate systems. For convenience, the angle of incidence of incoming electromagnetic radiation 205 and a surface normal, and the angle of reflection of scattered electromagnetic radiation 215 and the surface normal is described using the term $\theta_{spec}$. As the angle from the surface normal to the source is known, $\theta_{spec}$ is taken to be a known quantity.

Based on the geometry described above, the following relations may be written:

$$\frac{x_0 - x_{spec}}{z_0} = \tan\theta_{spec},$$

$x_0 = \rho_0 \sin\psi_0,$ $x_{spec} = \rho_{spec} \cos\psi_{spec}$, and $y_0 = y_{spec} = \rho_0 \sin\psi = \rho_{spec} \sin\psi_{spec}.$ From the above expressions, the following equation may be derived:

$\rho_{spec} \cos\psi_{spec} = -z_0 \tan\theta_{spec} \rho_0 \cos\psi_0$, and $\rho_{spec} \sin\psi_{spec} = \rho_0 \sin\psi_0.$ The following spot coordinates for the specular point may then be derived from the above equations and written as:

$$\tan\psi_{spec} = \frac{\rho_0 \sin\psi_0}{\rho_0 \cos\psi_0 - z\tan\theta_{spec}}$$

$\rho_{spec}^2 = \rho_0^2 - 2\rho_0 z_0 \cos\psi_0 \tan\theta_{spec} + z_0^2 \tan^2\theta_{spec}.$ The limits of the area integration for the BRDF may then be expressed in the spot coordinates: $0 \leq r \leq R$ where R is the spot radius, and $0 < \phi \leq 2\pi$. However, the BRDF integral separates into reflection coordinates. To simplify the BRDF integral, the limits of the area of integration may be expressed in the reflection coordinate system. To write such an expression, a transformation between spot coordinates and reflection coordinates is developed and is presently described.

A given reflection point in reflection coordinates may be written as (r, $\phi$). The Cartesian coordinates for a Cartesian system centered on the specular point are (x',y'). In spot coordinates, the specular point is ($\rho_{spec}$, $\phi_{spec}$)=($x_{spec}$, $y_{spec}$), wherein the unprimed (x,y) have their origin at the spot center. Then, an arbitrary point in the unprimed Cartesian system is $(x,y)=(x_{spec}, y_{spec})+(x',y')$ In terms of polar coordinates, this may be written as:

($\rho \cos\psi, \rho \sin\psi$)=($\rho_{spec} \cos\psi_{spec}+r \cos\phi, \rho_{spec} \sin\psi_{spec}+r \sin\phi$)

Recall that the limits of $\phi$ at a given $\rho$, such that $\rho \leq R$, are sought. That is, the limits remain inside illumination spot 600. Summing the squares of the x and y components provides the expression:

$\rho^2 = \rho_{spec}^2 + r^2 + \rho_{spec} r \cos\psi_{spec} \cos\phi + \rho_{spec} \sin\psi_{spec} r \sin\phi.$ The condition $\rho \leq R$ becomes $$\frac{R^2 - \rho_{spec}^2 - r^2}{\rho_{spec}^r} \geq \cos\psi_{spec}\cos\phi + \sin\psi_{spec}\sin\phi.$$

$\geq \cos\psi_{spec} \cos\phi + \sin\psi_{spec} \sin\phi.$

This is a transcendental equation, however, the equation may be solved numerically. The equation yields the coordinates of the points of intersection between a circle centered on the specular point and a circle centered on the illumination spot. There can be zero, one, or two such intersections. A parameter $\beta'=|\beta-\beta_0|$ is defined and an angular parameter $\alpha'$ is defined that follows constant $\beta'$ contours. $\alpha'$ is chosen to be equal to $\phi$. Therefore, $l(r)$ is the angular length of the arc between the solutions of $$\frac{R^2 - \rho_{spec}^2 - r^2}{\rho_{spec}^r} \geq \cos\psi_{spec}\cos\phi + \sin\psi_{spec}\sin\phi.$$

$$\geq \cos\psi_{spec}\cos\phi + \sin\psi_{spec}\sin\phi.$$

While the DSP and BRDF are written in terms of $|\beta-\beta_0|$, the coordinate transformations are written in terms of $r$. By design, the gradient of $|\beta-\beta_0|$ is aligned with $r$, so that $r$ may be written in term of $r=r(|\beta-\beta_0|)$ Furthermore, the geometry suggests that the transformation should be monotonic as $|\beta-\beta_0|=0$ is the center of the coordinate system.

The general form of the BRDF $$BRDF = \frac{1}{P_i}\frac{1}{\Omega_i}\int_{\Omega i}\int_{Area}\int_{\Omega d}\frac{d^2 P_i}{d\Omega_i dA}\frac{d p_d(\Omega_i,\Omega_d,A)}{d\Omega_d}d\Omega_i dA d\Omega_d$$

in view of the above coordinate transformations may be rewritten as:

$$BRDF = \iint \frac{dP}{dA}\frac{dp}{d\Omega}d\beta' d\alpha',$$

recall that $\beta'=|\beta-\beta_0|$, and $\alpha'$ is the angular parameter that follows the constant $\beta'$ contours. As the integrand is constant along direction $\beta'$, the integrand is parameterized by selecting $\alpha'=\phi$. The $\beta$ integral may then be written in terms of $r$, as long as a Jacobian is employed:

$$BRDF = \iint \frac{dP}{dA}\frac{dp}{d\Omega}\frac{d\beta'}{dr}dr d\phi.$$

$$\frac{d\beta'}{dr}$$

tend to be a relatively complicated expression and accordingly a simplification is sought. Without loss of generality, a relationship between $r$ and $|\beta-\beta_0|$ is developed for $\phi=0$ as $r$ depends only on $|\beta-\beta_0|$ and not on $\phi$, $$|\beta-\beta_0|=\beta'=\sqrt{\sin^2\theta+\sin^2\theta_0-2\sin\theta\sin\theta_0}.$$

$\theta_0$ may be taken as a known incidence angle and $\theta$ may be written in terms of trigonometric functions of the detector position altitude $z_0$ and the (variable) radius $r$:

$$\beta'^2 = \frac{z_0^2}{z_0^2+r^2} - \frac{2z_0\sin\theta_0}{\sqrt{z_0^2+r^2}} + \sin^2\theta_0.$$

The derivative $$\frac{d\beta'}{dr}$$

may be written as:

$$\frac{d\beta'}{dr} = \left(\frac{z_0^2}{z_0^2+r^2} - \frac{2z_0\sin\theta_0}{\sqrt{r^2+z_0^2}} + \sin^2\theta_0\right)^{-\frac{1}{2}}\left(\frac{z_0^2 r}{(z_0^2+r^2)} - \frac{z_0 r\sin\theta_0}{(z_0^2+r^2)^{(3/2)}}\right).$$

The simplified expression $$\frac{dp}{d\Omega} = \frac{1}{I_s l(r) r}\frac{dBDRF}{dr}$$

for the DSP derived above may now be written as:

$$\frac{dp}{d\Omega} = \frac{1}{I_s l(r) r}\left(\frac{d\beta'}{dr}\right)\frac{dBRDF}{d\beta'}.$$

Figure 7:
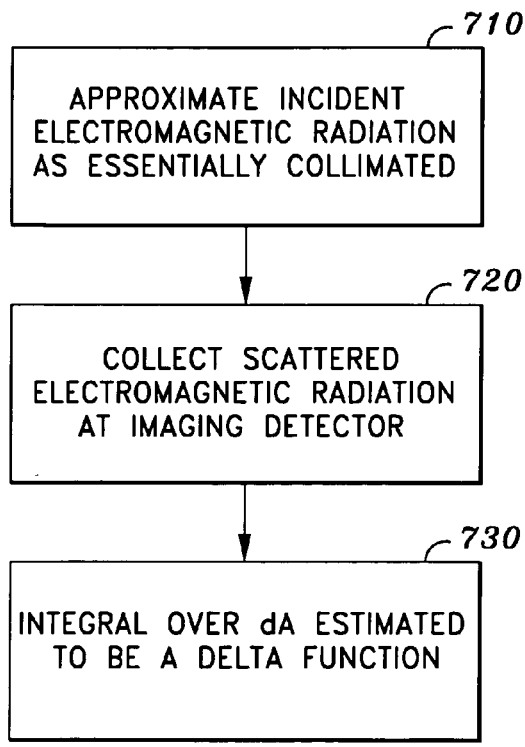
FIG. 7 is a high-level flow chart having steps for deconvolving a generalized BRDF expression according to another embodiment of the present invention.

FIG. 7 is a high-level flow chart having steps for deconvolving the generalized BRDF expression $$BRDF = \frac{1}{P_i}\frac{1}{\Omega_i}\int_{\Omega i}\int_{Area}\int_{\Omega d}\frac{d^2 P_i}{d\Omega_i dA}\frac{d p_d(\Omega_i,\Omega_d,A)}{d\Omega_d}d\Omega_i dA d\Omega_d$$

according to another embodiment of the present invention. It should be realized that the steps shown in FIG. 7 are not limiting on the invention as recited in the claims. Other techniques having fewer, substitute, and/or additional steps are within the purview of the invention and will be readily apparent to those of skill in the art. Similar to the embodiment outlined in the high-level flow chart shown in FIG. 3, at an initial step 700, incident electromagnetic radiation is approximated as being essentially collimated. From a physical optics point of view, this means that the rays of incident electromagnetic radiation 205 are essentially parallel. In view of this approximation, rays of incident electromagnetic radiation emanating from a unique differential solid angle $d\Omega_i$ are incident on a corresponding unique differential surface area dA. FIG. 4 shows rays 405 emanating from a unique differential solid angle 410, traveling essentially parallel, and being incident on a differential elements 420 of surface 202. As there is an essentially one-to-one relationship between unique differential source solid angles $d\Omega_i$ and unique differential surface area dA, the contribution to the BRDF from these differentials is a delta function for each unique differential source solid angles $d\Omega_i$ and corresponding unique differential surface area dA. Therefore, the integral over either the source solid angle or the integral over the surface area of the sample can be replaced with one. In the embodiment presently described, the integral over the source solid angle will be set to one. Setting the integral over the differential solid angle $d\Omega_i$ to one may be viewed as combining the integral of the differential solid angle $d\Omega_i$ and the differential surface area dA due to the interdependency of these differentials from the collimation assumption.

As the integral over the differential solid angle $d\Omega_i$ has been set to one, the expression for the BRDF has been reduced to a four dimensional integral that may be written as $$BRDF = \frac{1}{P_i}\frac{1}{\Omega_i}\int_{Area}\int_{\Omega d}\frac{dP_i}{dA}\frac{d\,p_d(\Omega_i, \Omega_d, A)}{d\,\Omega_d}dA\,d\Omega_d.$$

At 710, an imaging detector is assumed to collect scattered electromagnetic radiation 215 scattered from surface 410. An imaging detector is configured to collect radiation scattered from each surface element dA on the sample surface 202. As light from each surface element dA is collected by the imaging detector, collected light may be localized to a very small area on the sample. Accordingly, the integral dA over the surface may be estimated as a delta function, step 720. That is, the integral over the surface may be replaced with one. The remaining integral is over the scattering solid angle $d\Omega_d$ and may be written as:

$$BRDF = \frac{1}{P_i}\frac{1}{\Omega_i}\int_{\Omega d}\left(\frac{d\,p_d|\beta - \beta_0|}{d\,\Omega_d}\right)\sin\theta_d\,d\theta_d\,d\phi_d$$

A primary aperture of the imaging detector can be described as a set of points $(\theta,\phi)$ in spherical coordinates that are centered on the sample origin O. As $(\beta-\beta_0)$ is a function of the set of pointes $(\theta,\phi)$, the angles $\theta$ and $\phi$, as well as the constant incident light angles, a coordinate system may be construct across the primary aperture, such that one coordinate follows lines of constant $|\beta-\beta_0|$, while the other is perpendicular to the lines of constant $|\beta-\beta_0|$. A coordinate $k_1$ is defined to be the coordinate that follows lines of constants $|\beta-\beta_0|$, and a coordinate $k_2$ is defined to be the coordinate perpendicular to the lines of constant $|\beta-\beta_0|$. Accordingly, $k_2$ may simply be written as $k_2=|\beta-\beta_0|$. Constant $|\beta-\beta_0|$ implies that equation $|\beta-\beta_0|=\beta'=\sqrt{\sin^2\theta+\sin^2\theta_0-2\sin\theta\sin\theta_0}$ may be written as $\sin^2\theta = 2\sin\theta\sin\theta_0\cos\Delta\phi + C.$ $k_1$ is, therefore, set equal to $\sin^2\theta$. The Jacobian $J(k_1,k_2)$ is calculated to cast the BRDF into the coordinates $k_1$ and $k_2$. The BRDF may then be written in terms $k_1$ and $k_2$ as:

$$BRDF = \int_{D^*}\frac{d\,p(|\beta-\beta_0|)}{d\Omega}\sqrt{k_1}\left|\frac{\partial(\theta, \phi)}{\partial(k_1 k_2)}\right|dk_1 dk_k.$$

$D^*$ represents the area of the primary aperture of the imaging detector and is suitably described in terms of the coordinates $k_1$ and $k_2$. The Jacobian $J(k_1,k_2)$ may be calculated in a customary manner, such as that described in Vector Calculus 4th edition, by J. E. Marsden and A. H. Trombda, published by W H Freeman & Co. Apr. 1996, at pages 372–376.

From the definition of $k_1$, $\theta$ may be written as $\theta=\cos^{-1}\sqrt{k_1}\Delta\phi$. $\phi$ may be extracted, resulting in the relationship:

$$\Delta\phi = \cos^{-1}\left(\frac{-k_2 + k_1 + \sin^2\theta_0}{2\sqrt{k_1}\sin\theta_0}\right).$$

The derivative $$\frac{\partial\theta}{\partial k_2} = 0,$$

therefore, $$\frac{\partial\phi}{\partial k_1}$$

need not be calculated. The derivative $$\frac{\partial\theta}{\partial k_1}$$

is $$\frac{\partial\theta}{\partial k_1} = \frac{1}{2\sqrt{k(1-k)}},$$

and the derivative $$\frac{\partial\phi}{\partial k_2}$$

is $$\frac{\partial\phi}{\partial k_2} = \sqrt{4k_1\sin^4\theta_0 - (k_1 - k_2 + \sin^2\theta_0)^2}.$$

The Jacobian is just the product of the derivatives $$\frac{\partial\phi}{\partial k_1}$$

and $$\frac{\partial \phi}{\partial k_1},$$

since the other term was eliminated by $$\frac{\partial \theta}{\partial k_2} = 0,$$

and may be written as follows:

$$J(k_1 k_2) = \left| \frac{\partial(\theta, \phi)}{\partial(k_1, k_2)} \right| = \left( 2\sqrt{k_1(1-k_1)(4k_1\sin^4\theta_0 - (k_1 - k_2 + \sin^2\theta_0)^2)} \right)^{-1}$$

Thus, the expression for the BRDF may be written as:

$$BRDF = \int_{k_2} \frac{d\,p(|\beta - \beta_0|)}{d\Omega} \left[ \int_{k_1 = f(k_2)}^{k_1 = g(k_2)} \sqrt{k_1}\, J(k_1, k_2)\, dk_1 \right] dk_2.$$

The limits f and g are those values, for a given $k_2$, where the contour of $|\beta-\beta_0|$ intersects the edge of the primary aperture. That is, if $(\theta_1,\phi_1)$ is the center of the aperture, then $(\theta_2,\phi_2)$ is sought, such that $$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha,$$

wherein, $\alpha$ is the half-angle of the aperture as viewed from the sample. Expressions for $\theta$ and $\phi$ in terms of $k_1$ and $k_2$ are given above, and the resulting transcendental equation can be solved numerically for a given value of $k_2$. Next, the integral over $k_1$ can be solved numerically, for a given value of $k_2$. The BRDF curve is differenced, giving the approximation:

$$\frac{d\,BRDF(k_2)}{dk_2} = \frac{d\,p(k_2)}{d\Omega} \mathcal{K}(k_2),$$

wherein $\mathcal{K}$ is the integral over $k_1$:

$$k = \int_{k_1 = f(k_2)}^{k_1 = g(k_2)} \sqrt{k_1}\, J(k_1, k_2)\, dk_1$$

Figure 8:
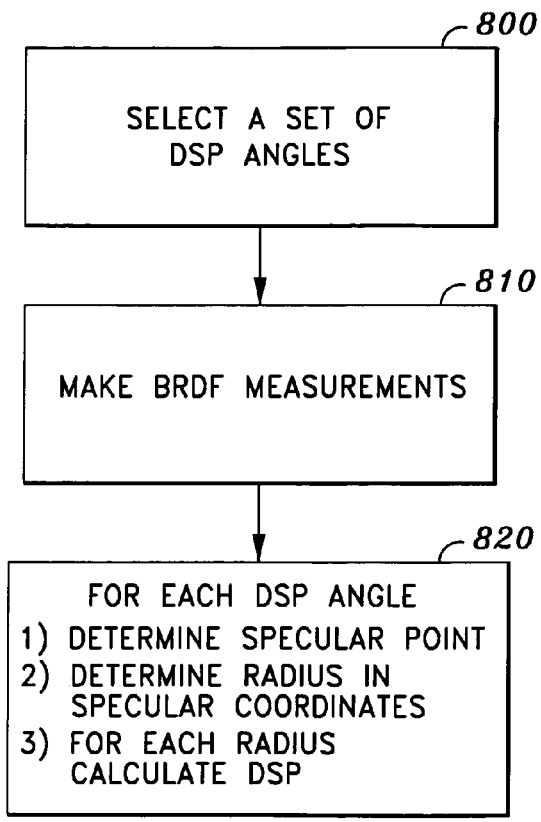
FIG. 8 is a high-level flow chart having steps for deconvolving BRDF measurements to generate a distribution-scattering profile (DSP) according to an embodiment of the present invention.

The following description provides a discussion of a method for implementing the above equations for point detectors and imaging detectors to generate a DSP from measured BRDFs. A method for implementing the above equation for a point detector is described in combination with FIG. 8, which shows a high-level flow chart having steps for implementing the method according to an embodiment of the present invention. It should be realized that the steps shown in FIG. 8 are not limiting on the invention as recited in the claims. Other techniques having fewer, substitute, and/or additional steps are within the purview of the invention and will be readily apparent to those of skill in the art. To implement the described method for a point detector, such as a photomultiplier tube, measured BRDF data is converted to an equivalent DSP. Input data for the method is measured BRDF data at a set of angles, and the output is a calculated DSP at a set of desired angles.

At 800, the set of desired DSP angles are selected. At 810, BRDF measurements are made. The measurements may be made at a specified angular resolution, either by measurement or interpolation. At 820, for each desired DSP angle: (a) a location of the specular point is determined, in spot coordinates, making use of equations:

$$\tan \psi_{spec} = \frac{\rho_0 \sin \psi_0}{\rho_0 \cos \psi_0 - z \tan \theta_{spec}},$$

$$\rho_{spec}^2 = \rho_0^2 - 2\rho_0 z_0 \cos \psi_0 \tan \theta_{spec} + z_0^2 \tan^2 \theta_{spec}$$

which are described in detail above; (b) a radius in specular coordinates for each value of $|\beta-\beta_0|$ that has been measured is determined; and (c) at each of the radii
 i. dBRDF/dβ is approximated by differencing appropriate measured values of BRDF,
 ii.

$$\frac{\partial \beta}{\partial r}$$

is calculated making use of equation:

$$\frac{d\beta'}{dr} = \left( \frac{z_0^2}{z_0^2 + r^2} - \frac{2z_0 \sin\theta_0}{\sqrt{r^2 + z_0^2}} + \sin^2\theta_0 \right)^{-\frac{1}{2}} \left( \frac{z_0^2 r}{(z_0^2 + r^2)} - \frac{z_0 r \sin\theta_0}{(z_0^2 + r^2)^{(3/2)}} \right),$$

iii. l(r) is calculated by numerically finding the zeros of equation:

$$\frac{R^2 - \rho_{spec}^2 - r^2}{\rho_{spec} r}$$

$\geq \cos\psi_{spec} \cos\phi + \sin\psi_{spec} \sin\phi$, and
 iv. the DSP at r is calculated making use of equation:

$$\frac{d\rho}{d\Omega} = \frac{1}{I_s l(r) r} \left( \frac{d\beta'}{dr} \right) \frac{d\,BRDF}{d\beta'}.$$

Each of the above equation in steps (a), (b), and (c) listed above is described in detail in above.

Figure 9:
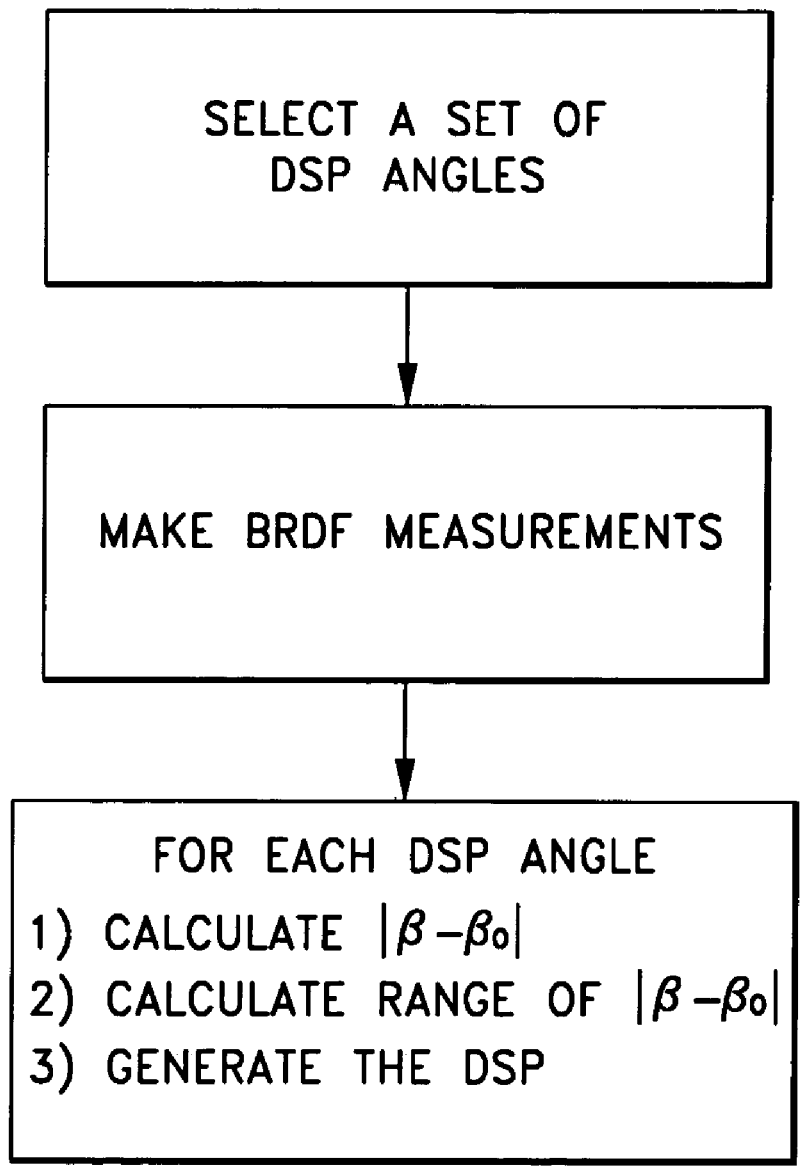
FIG. 9 is a high-level flow chart having steps for deconvolving BRDF measurements to generate a DSP according to another embodiment of the present invention.

A method for implementing the above equation for an image detector, such as a single pixel of CCD array or CMOS array, is described in combination with FIG. 9, which shows a high-level flow chart having steps for implementing the method according to an embodiment of the present invention. It should be realized that the steps shown in FIG. 9 are not limiting on the invention as recited in the claims. Other techniques having fewer, substitute, and/or additional steps are within the purview of the invention and will be readily apparent to those of skill in the art. Similar to the method described above for a point detector, measured BRDF data is converted to an equivalent DSP. The input data is the measured BRDF at a particular pixel of an image of the sample, at a set of primary aperture angles, and the output is a calculated DSP at an arbitrary set of desired angles.

At 900, the set of desired DSP angles are selected. At 910, BRDF measurements are made. The measurements may be made at a specified angular resolution, either by measurement or interpolation. At 920, for each desired DSP angle: (a) calculate the value of $|\beta-\beta_0|$ in the center of a primary aperture of the image detector; (b) calculate the range of $|\beta-\beta_0|$ present on the primary aperture, as described by the equations $$\tan \psi_{spec} = \frac{\rho_0 \sin \psi_0}{\rho_0 \cos \psi_0 - z \tan \theta_{spec}},$$

; and $$\rho_{spec}^2 = \rho_0^2 - 2\rho_0 z_0 \cos \psi_0 \tan \theta_{spec} + z_0^2 \tan^2 \theta_{spec}$$

(c) for each value of $|\beta-\beta_0|$ (sufficiently spaced to measure the desired DSP angles):
 i. approximate $dBRDF/d\beta$ by differencing relevant measured values of BRDF,
 ii. calculate the limits of the BRDF integral by numerically solving the equation:

$$\cos^{-1}(\sin \theta_1 \cos \phi_1 \sin \theta_2 \cos \phi_2 + \sin \theta_1 \sin \phi_1 \sin \theta_2 \sin \phi_2 + \cos \theta_1 \cos \theta_2) \leq \alpha$$

iii. calculate $\mathcal{K}$ making use of equation:

$$k = \int_{k_1=f(k_2)}^{k_1=g(k_2)} \sqrt{k_1} J(k_1, k_2) dk_1,\text{ and}$$

iv. solve equation:

$$\frac{d BRDF(k_2)}{dk_2} = \frac{d p(k_2)}{d\Omega}$$

$\kappa(k_2)$ to generate the DSP.

Each of the above equation in steps (a), (b), and (c) listed above is described in detail in above detailed descriptions above.

Figure 10:
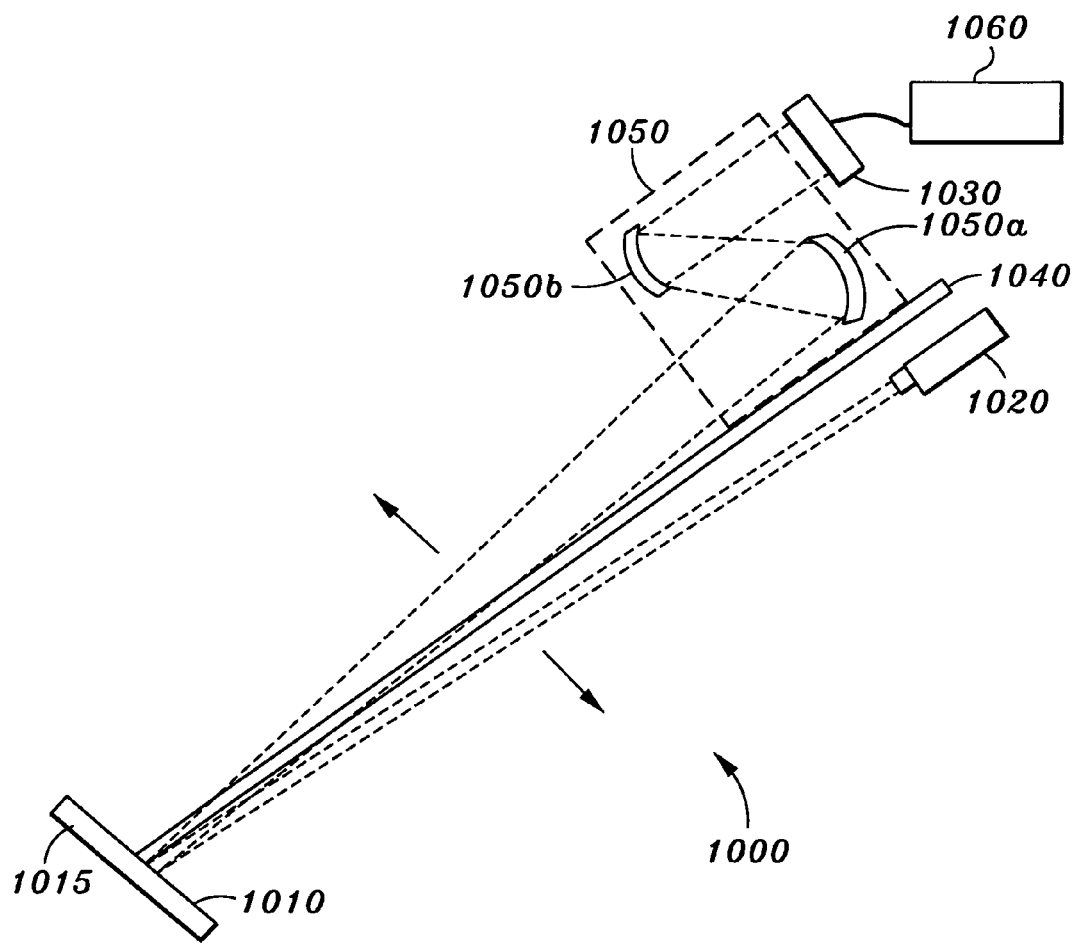
FIG. 10 shows an optical system in which embodiments of the invention may be implemented.

FIG. 10 shows an optical collection system 1000 in which embodiments of the invention may be implemented. Optical collection system 1000 may be configured to collect BRDF data for calculating a DSP of a sample surface 1010 of a sample 1015. Optical collection system 1000 may include an illumination source 1020 configured to illuminate a sample with a substantially collimated beam. Illumination source 1020 may be a laser, a mercury vapor lamp, xenon arc lamp, or the like, and may include optical elements configured to spread electromagnetic radiation from the illumination source sufficiently widely to illuminate all or a portion of sample surface 1010. A detector 1030 may be disposed on an extended beam 1040 that is configured to sweep through a variety of angles to collect scattered electromagnetic radiation at the variety of angles. According to one embodiment, detector 1030 is a CCD array or a CMOS array. According to one embodiment, extended beam 1040 is between about ten meters and about 30 meters in length, and according to a specific embodiment is about 20 meters in length. The extended beam may be configured to rotate in angular steps of about 0.05° or more, and according to a specific embodiment may be configured to rotate in about 0.1° steps.

A focusing module 1050 may be used to collect scattered light into a given reflection angle $\theta_d$ to detector 1030. According to one embodiment, focusing module 1050 includes first and second mirrors 1050a, and 1050b, respectively. Mirrors 1050a and 1050b may be parabolic mirrors and may form a Cassegrain telescope, which has a focal plane that approximately coincides with a collector plane of detector 1030. As the focal plane coincides with the collector plane, the formed Cassegrain telescope forms images of the sample surface at the image plane. Mirrors 1050a and 105b may be configured as off axis mirrors to optimize light directed to the detector. That is, mirror 1050b, which may be configured to form a secondary mirror of a telescope, is disposed so as not to block light collected by the mirror 1050a, which is configured to form a primary mirror of the telescope. According to one embodiment, mirror 1050a subtends an angle of about $8.3 \times 10^{-4}$ radians or 0.048°. According to another embodiment, mirror 1050a subtends an angle of about $2.5 \times 10^{-2}$ radians or 1.4°. According to one embodiment, detector 1030 is configured to direct collected electromagnetic radiation to a computation module 1060 configured to calculate a DSP from the collected BRDF data.

Figure 11:
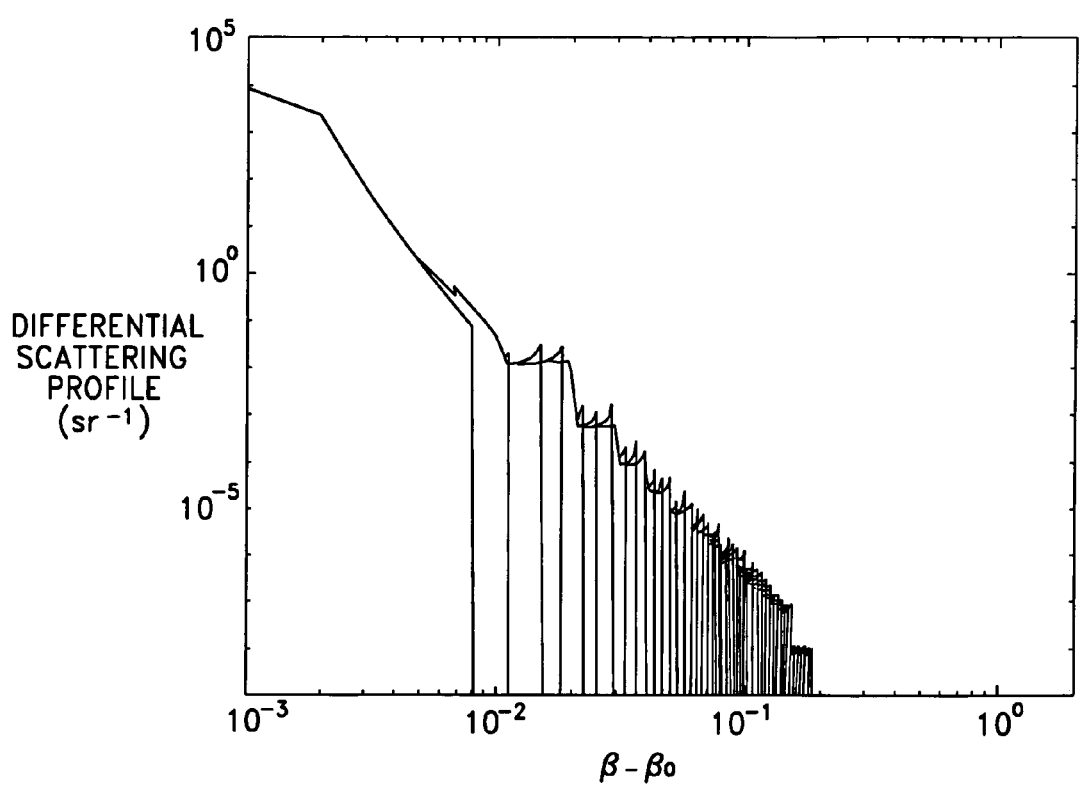
FIG. 11 shows an example of a DSP that may be calculated from interpolated BRDF data according to an embodiment of the present invention.
Figure 12:
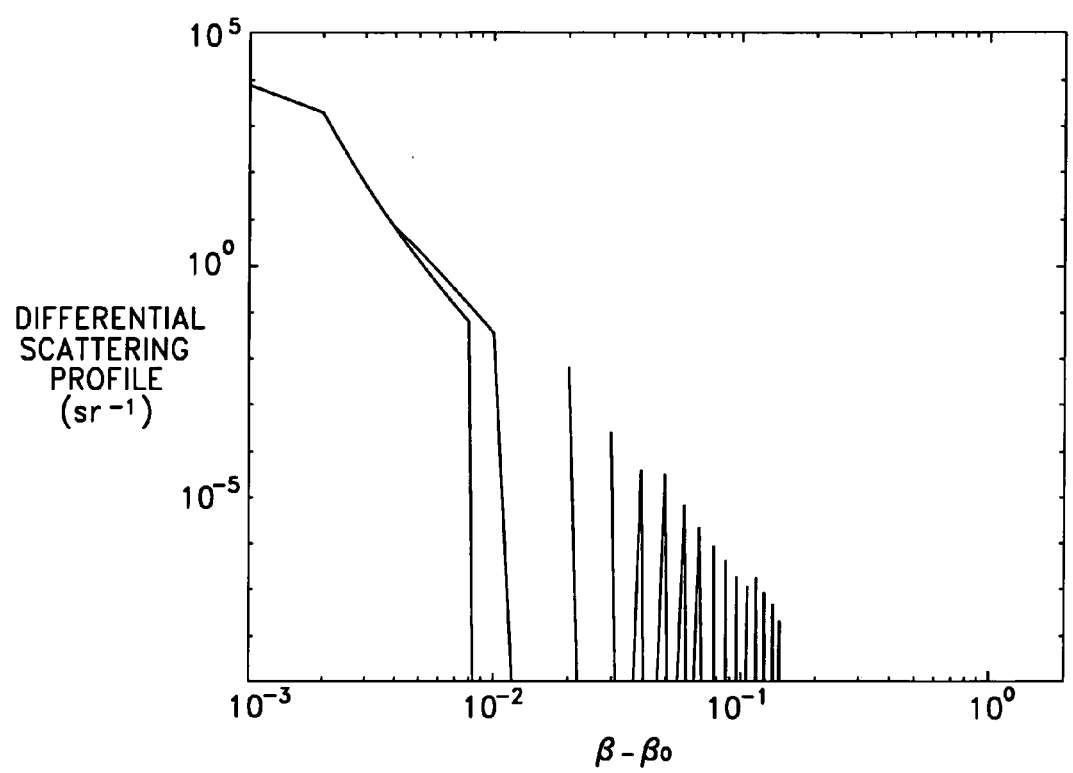
FIG. 12 shows another example of a DSP that may be calculated from non-interpolated BRDF data according to another embodiment of the present invention.

FIG. 11 shows an example of a DSP that may be calculated according to embodiments of the present invention. Primary mirror 1050a may be positioned in a number of overlapping positions and measurements made at each overlapping position in sequence. Collected data may be used to achieve a complete deconvolution. The DSP shown in FIG. 11 may be generated, for example by interpolating between BRDF measurements. Mismatches in the DSP may due to BRDF interpolations made in measured BRDF data. Alternatively, the DSP may be calculated from BRDF data that is not interpolated. FIG. 12 shows an example DSP generated from the same BRDF data used to generate the DSP in FIG. 11, however, the BRDF data used to calculate the DSP of FIG. 12 was not interpolated.

BRDF measurements from which calculated the DSPs (shown in FIGS. 11 and 12) may be calculated are described below. A substantially collimated beam may be incident on a sample surface at near-normal incidence (see FIG. 10), such that $|\beta-\beta_0|=0$ occurs at nearly the same point as $\theta=0$. In such configuration, $|\beta-\beta_0|$ is approximated by $\theta-\theta_{spec}$. A 2" target spot subtends an angle of 0.48° (i.e., $8.3 \times 10^{-3}$ radians) from a detector positioned 20 feet away, for example, on boom 1040. To collect 5 data points within 0.48° degrees, BRDF measurements may be made at 0.12° increments. For more accuracy, greater than 5 BRDF measurements may be made, for example, 10 BRDF measurements may be may at 0.053° increments. For an incident angle at approximately 45°, near-specular measurement density changes by a factor of $1/\cos \theta = \sqrt{2}$. It is noted that these densities of BRDF measurements are sufficient for convergence of the deconvolution, however, to get resolution on rapid changes of the DSP finer BRDF measures may be made.

Measurement variations (or uncertainties) may constrain the quality of the DSPs that are extrapolated from measured BRDFs. Calculated DSP may be affected by measurement uncertainty in the scattering angle $\theta$, noise in the power measured by the camera, pixilation uncertainty in the solid angle used for the BRDF calculation, uncertainty in the out-of-plane angle $\phi$, and variations in the source power due to fluctuations in source or differences in the neutral density filters used to filter source radiation.

An expression for the DSP uncertainty, which is introduced by uncertainty in the scattering angle, is generated via the chain rule by $$\delta_\theta DSP = \frac{\partial DSP}{\partial \beta'} \frac{\partial \beta'}{\partial \theta} \delta \theta,$$

wherein $\beta'=|\beta-\beta_0|$ ($\beta'$ is introduced for convenience of notation). This uncertainty may be introduced either by uncertainties in the beam positions or by uncertainties in the sample angles.

For a sample that is a Harvey-Shack material (see Harvey '76) with a power law DSP, the DSP is:

$$DSP = m\beta'^{-\gamma},$$

such that $$\frac{\partial DSP}{\partial \beta'}$$

$$= -\gamma m \beta'^{-\gamma-1}.$$

By definition, $$|\beta-\beta_0| = (\sin^2 \theta + \sin^2 \theta_0 - 2 \sin \theta \sin \theta_0 \cos \Delta\phi)^{1/2},$$

therefore, $$\frac{\partial \beta'}{\partial \theta} = \frac{-\cos \theta}{\beta'}$$

$$(\sin \theta - \sin \theta_0 \cos \Delta\phi).$$

Therefore, the relative uncertainty in the DSP may be written as:

$$\frac{\delta_\theta DSP}{DSP} = \frac{\gamma m \beta'^{-\gamma-1} \cos \theta (\sin \theta - \sin \theta_0 \cos \Delta\phi)}{m \beta'^{-\gamma-1}} \delta\theta =$$

$$\frac{\gamma \cos \theta (\sin \theta - \sin \theta_0 \cos \Delta\phi)}{\beta'^2} \delta\theta.$$

In the special case when $\Delta\phi$ is zero, $|\beta-\beta_0|=\sin \theta - \sin \theta_0$, the relative uncertainty in the DSP may be written as:

$$\frac{\delta\theta DSP}{DSP} = \frac{\gamma \cos \theta}{\sin \theta - \sin \theta_0} \delta\theta.$$

Table 1 shows relative uncertainty in DSP for a power-law index of $\gamma=6$ and an incident angle of $\theta_0$ is about 45°. The angular uncertainty is a function of the incident angle at constant $|\beta-\beta_0|$. The relative uncertainty is within an acceptable margin for $\delta=0.001$. According to one embodiment, $\delta=0.001$ corresponds to approximately seven pixel widths (e.g.; CCD or CMOS pixel widths) of detector 1030. According to one embodiment, pixel widths are approximately 13 microns. Table shows the relative uncertainties in the DSP as a function of the incident angle and the angular error for such a configuration.

In a configuration in which $\phi$ is the vertical displacement $\delta_\phi$ DSP may be estimated. That is, $$\frac{\partial \beta'}{\partial \phi} = \frac{\sqrt{2 \sin \theta \sin \theta_0 \sin \phi}}{\beta'},$$

such that $$\frac{\delta_\phi DSP}{DSP} = \frac{\gamma}{\beta'} \sqrt{2 \sin \theta \sin \theta_0 \sin \phi \delta\phi}.$$

TABLE 1

|  | =0 | 5 | 0 | 0 | 4.5 | 4.9 | 4.95 |
|---|---|---|---|---|---|---|---|
| $\delta = 0.001$ | .015% | .023% | .044% | .125% | .21% | .01% | 2% |
| 0.003 | .044% | .068% | .131% | .374% | .6% | 8.0% | 6% |
| 0.005 | .074% | .113% | .219% | .624% | .0% | 0.0% | 0% |
| 0.008 | .118% | .181% | .350% | .998% | .6% | 8% | 6% |
| 0.01 | .148% | .226% | .438% | .247% | 2% | 0% | 20% |

Uncertainty in a CCD array response may affect the DSP measurement in two ways. First, inaccurate CCD response can directly alter measured power, and thus change the calculated DSP. Second, a first-order uncertainty may be introduced by uncertainties in the matching algorithm. If variations in CCD response lead to uncertainties in matching the positions of adjacent frames, an effective scattering-angle uncertainty may result.

It should also be understood that the examples and embodiments described herein are for illustrative purposes only and that various modifications or changes in view thereof will be suggested to persons skilled in the art and are to be included within the spirit and purview of this application and scope of the appended claims. Therefore, the above description should not be taken as limiting the scope of the invention as defined by the claims. All publications, patents, and patent applications cited herein are hereby incorporated by reference for all purposes in their entirety.

What is claimed is:

1. A computerized method for estimating scattering of electromagnetic radiation from a surface, the method comprising:
    providing a distribution expression that includes a first integral over a source solid angle, a second integral over a sample area, third integral over detector solid angle, and an integrand that includes a differential-scattering profile;
    approximating the first and second integrals to be the second integral, wherein the source electromagnetic radiation is approximated to be collimated;
    approximating the second and third integral to be the third integral, wherein a detector for detecting the electromagnetic radiation scattered from the surface is approximated to be a point detector;
    transforming the coordinates of the third integral over detector solid angle to first and second dimensions in cosine space to form a fourth integral, wherein the surface is approximated to be shift invariant;
    integrating over the first dimension of the fourth integral;

differentiating the fourth integral with respect to the second dimension to generate the differential-scattering profile; and generating an optical system design based on the differential-scattering profile.

2. The method of claim 1, wherein the distribution expression includes a bidirectional reflectance distribution function (BRDF).

3. The method of claim 2, wherein the bidirectional reflectance distribution function may be represented by the equation:

$$BRDF = \frac{1}{P_i}\frac{1}{\Omega_i}\int_{\Omega_i}\int_{Ares}\int_{\Omega_d}\frac{d^2 P_i}{d\Omega_i dA}\frac{dp_d(\Omega_i, \Omega_d, A)}{d\Omega_d}d\Omega_i dA\, d\Omega_d,$$

wherein:
the integral with respect to $d\Omega_i$ is the first integral,
the integral with respect to $dA$ is the second integral,
the integral with respect to $d\Omega_d$ is the third integral,
the expression $$\frac{dp_d(\Omega_i, \Omega_d, A)}{d\Omega_d}$$

is the differential scattering profile, and
$P_i$ is incident power of the electromagnetic radiation.

4. The method of claim 1, further comprising generating an empirical-differential-scattering profile from measured data of electromagnetic radiation scattering from a physical surface corresponding to the surface, a difference of the empirical-differential-scattering profile and the differential-scattering profile being less than about ten percent.

5. The method of claim 1, wherein the differential-scattering profile is a continuous solution representing an algebraic model of specular scattering and non-specular scattering of the electromagnetic radiation from the surface.

6. The method of claim 1, wherein lines of constant-scattering intensity are co-centric circles in cosine space.

7. The method of claim 6, wherein the first dimension in cosine space is a radial dimension perpendicular to the co-centric circles.

8. The method of claim 7, wherein the second dimension is a circular dimension following the co-centric circles.

9. The method of claim 6, wherein the first dimension is a circular dimension following the co-centric circles.

10. The method of claim 9, wherein the second dimension in cosine space is a radial dimension perpendicular to the co-centric circles.

11. The method of claim 6, wherein the co-centric circles are lines of constant $|\beta-\beta_0|$.

12. The method of claim 11, wherein $|\beta-\beta_0|=(\sin^2 \theta_i+\sin^2 \theta_d-2 \sin^2 \theta_i \sin^2 \theta_d \cos \Delta\phi)^{1/2}$.

13. The method of claim 12, further comprising estimating $|\beta-\beta_0|=\theta_i+\theta_d$ for relatively small angle approximations of $\theta_i$ and for $\Delta\phi$ being approximately zero.

14. The method of claim 1, wherein the fourth integral may be represented by the expression:

$$BRDF = \int_{D'} \frac{dp(|\beta-\beta_0|)}{d\Omega}\sqrt{k_1}\left|\frac{\partial(\theta,\phi)}{\partial(k_1 k_2)}\right|dk_1 dk_2,$$

wherein:
$k_1$ is a coordinate in cosine space and follows lines of constant $|\beta-\beta_0|$;
$k_2$ is another coordinate in cosine space that is perpendicular to lines of constant $|\beta-\beta_0|$; and $$|\beta-\beta_0|=\sqrt{\sin^2\theta+\sin^2\theta_0-2\sin\theta\sin\theta_0}.$$

15. The method of claim 1, wherein the differentiating step includes deconvolving the fourth integral.

16. The method of claim 1, wherein the step of approximating the first and second integrals to be the second integral includes approximating a one-to-one correspondence between a differential element of the source electromagnetic radiation and a differential surface area of the surface.

17. The method of claim 1, wherein the step of approximating the second and third integral to be the third integral includes approximating that electromagnetic scattered from a differential surface area sources is incident on the point detector.

18. The method of claim 1, fourth comprising using the differential-scattering profile to reduce scattering in the optical system design.

19. The method of claim 1, further comprising using the differential-scattering profile to compensate for scattering in the optical system design.

20. The method of claim 1, wherein the optical system design includes a design for computer generated graphic.

21. A computerized method for estimating scattering of electromagnetic radiation from a surface, the method comprising:
providing a distribution expression that includes a first integral over source solid angle, a second integral over a sample area, a third integral over detector solid angle, and an integrand that includes a differential-scattering profile;
approximating the first and second integrals to be the second integral, wherein source electromagnetic radiation is approximated to be collimated,
approximating third integral to be one based on detecting the electromagnetic radiation scattered from the surface at an imaging detector;
transforming the coordinates of the second integral over the sample area to first and second dimensions in cosine space to form a fourth integral, wherein the surface is approximated to be shift invariant;
integrating over the first dimension of the fourth integral;
differentiating the fourth integral with respect to the second dimension to generate the differential-scattering profile; and
generating an optical system design based on the differential-scatting profile.

22. The method of claim 21, further comprising implementing the differential-scattering profile to reduce scattering in the optical system design.

23. The method of claim 21, further comprising using the differential-scattering profile to compensate for scattering in the optical system design.

24. The method of claim 21 further comprising using the differential-scattering profile to simulate scattering in a computer generated graphic.

25. The method of claim 24, wherein the optical system design includes the computer generated graphic.

26. The method of claim 21, further comprising implementing the differential-scattering profile to simulate scattering from a physical surface.

27. An optical system comprising:
a collimated beam of electromagnetic radiation configured to illuminate a sample surface, the sample surface being shift invariant;
an imaging detector configured to collect electromagnetic radiation scattered from the sample surface, the imaging detector configured to collect the scattered electromagnetic radiation at a plurality of scattering angles to generate a scattering profile; and
a computer device configured to generate an estimated differential-scattering profile and compare the scattering profile and the estimated-differential-scattering profile to generate an optical system design, wherein the estimated-differential-scattering profile is a continuous solution of an differential model of spectral scattering and non-spectral scattering derived from a deconvolution of a bidirectional reflectance distribution function (BRDF),
wherein:
an expression for the BRDF includes a first integral over a source solid angle, a second integral over the sample surface, a third integral over detector solid angle, and an integrand that includes the estimated-differential-scattering profile;
the first and second integrals are approximated to be the second integral based on the source electromagnetic radiation being in the form of the collimated beam;
the third integral is approximated to be one based on the detector being an imaging detector;
the second integral is transformed from an integral over detector solid angle to a fourth integral over first and second dimensions in cosine space based on the sample surface being shift invariant; and
the fourth integral is integrated with respect to the first dimension and deconvolved with respect to the second dimension to generate the estimated differential-scattering profile.

28. The optical system of claim 27, wherein a difference between the scattering profile and the estimated differential-scattering profile is less than or equal to about ten percent.

29. The optical system of claim 27, wherein the estimated-differential-scattering profile is configured to be used to reduce scattering in the optical system design.

30. The optical system of claim 27, wherein the estimated-differential-scattering profile is configured to be used to compensate for scattering in the optical system design.

31. The optical system of claim 27, wherein the estimated-differential-scattering profile is configured to be used to simulate scattering in a computer generated graphic.

32. The optical system of claim 27, wherein the optical system design includes a computer generated graphic.

* * * * *

UNITED STATES PATENT AND TRADEMARK OFFICE
CERTIFICATE OF CORRECTION

PATENT NO. : 7,119,903 B1
APPLICATION NO. : 10/692704
DATED : October 10, 2006
INVENTOR(S) : Brian B. Jones It is certified that error appears in the above-identified patent and that said Letters Patent is hereby corrected as shown below:

IN THE SPECIFICATION:

Column 6, Line 55: remove "(i.e.," after "integrand"

Column 10, line 20, replace: "$\rho_{spec}{}^2 = \rho_0{}^2 - 2\rho_0 z_0 \cos\psi_0 \tan\theta_{spec} + z_0{}^2 \tan^2\theta_{spec}.$"
with: --$\rho_{spec}^2 = \rho_0^2 - 2\rho_0 z_0 \cos\psi_0 \tan\theta_{spec} + z_0^2 \tan^2\theta_{spec}.$--

Column 10, line 22, replace: "$0 \leq r \leqq R$" with --$0 < r \leq R$--

Column 10, line 23, replace: "$0 < \phi \leqq 2\pi.$" with --$0 < \phi \leq 2\pi.$--

Column 10, line 49, replace: "$\rho^2 = \rho_{spec}{}^2 + r^2 + \rho_{spec} r \cos\psi_{spec} \cos\phi + \rho_{spec} \sin\psi_{spec} r \sin\phi.$"

with: --$\rho^2 = \rho_{spec}^2 + r^2 + \rho_{spec} r \cos\psi_{spec} \cos\phi + \rho_{spec} \sin\psi_{spec} r \sin\phi.$--

Column 10, line 52, replace: "$\rho \leqq R$" with --$\rho \leq R$--

Column 10, line 55, replace: "$\dfrac{R^2 - \rho_{spec}^2 - r^2}{\rho_{spec}^r} \geq \cos\psi_{spec} \cos\phi + \sin\psi_{spec} \sin\phi.$"

with: --$\dfrac{R^2 - \rho_{spec}^2 - r^2}{\rho_{spec} r} \geq \cos\psi_{spec} \cos\phi + \sin\psi_{spec} \sin\phi.$--

Column 10, line 59, delete equation: "$\geqq \cos\psi_{spec}\cos\phi + \sin\psi_{spec} \sin\phi.$"

Column 11, line 5, replace: "$\dfrac{R^2 - \rho_{spec}^2 - r^2}{\rho_{spec}^r} \geq \cos\psi_{spec} \cos\phi + \sin\psi_{spec} \sin\phi.$"

with: --$\dfrac{R^2 - \rho_{spec}^2 - r^2}{\rho_{spec} r} \geq \cos\psi_{spec} \cos\phi + \sin\psi_{spec} \sin\phi.$--

UNITED STATES PATENT AND TRADEMARK OFFICE
CERTIFICATE OF CORRECTION

PATENT NO. : 7,119,903 B1  
APPLICATION NO. : 10/692704  
DATED : October 10, 2006  
INVENTOR(S) : Brian B. Jones Page 2 of 4

It is certified that error appears in the above-identified patent and that said Letters Patent is hereby corrected as shown below:

Column 11, line 10, delete equation: "$\geq \cos\psi_{spec} \cos\phi + \sin\psi_{spec}  \beta'^2 = \frac{z_0^2}{z_0^2 + r^2} - \frac{2z_0 \sin\theta_0}{\sqrt{z_0^2 + r^2}} + \sin^2\theta_0 \sin\phi.$"

Column 12, line 7, replace: " $\beta'^2 = \frac{z_0^2}{z_0^2 + r^2} - \frac{2z_0 \sin\theta_0}{\sqrt{z_0^2 + r^2}} + \sin^2\theta_0$ "

with: --
$$\frac{d\beta'}{dr} = \left( \frac{z_0^2}{z_0^2 + r^2} - \frac{2z_0 \sin\theta_0}{\sqrt{z_0^2 + r^2}} + \sin^2\theta_0 \right)^{-\frac{1}{2}} \left( \frac{z_0^2 r}{(z_0^2 + r^2)} - \frac{z_0 r \sin\theta_0}{(z_0^2 + r^2)^{(3/2)}} \right)$$
--

Column 12, line 20, replace:

" $\frac{d\beta'}{dr} = \left( \frac{z_0^2}{z_0^2 + r^2} - \frac{2z_0 \sin\theta_0}{\sqrt{r^2 + z_0^2}} + \sin^2\theta_0 \right)^{-\frac{1}{2}} \left( \frac{z_0^2 r}{(z_0^2 + r^2)} - \frac{z_0 r \sin\theta_0}{(z_0^2 + r^2)^{(3/2)}} \right)$ "

with: --
$$\frac{dp}{d\Omega} = \frac{1}{I_s l(r) r} \left( \frac{d\beta'}{dr} \right) \frac{dBRDF}{d\beta'}.$$
--

Column 12, line 37, replace: " $\frac{dp}{d\Omega} = \frac{1}{I_s \ell(r) r} \left( \frac{d\beta'}{dr} \right) \frac{dBRDF}{d\beta'}.$
$\int_{D^*} \frac{dp(|\beta - \beta_0|)}{d\Omega} \sqrt{k_1} \left| \frac{\partial(\theta, \phi)}{\partial(k_1 k_2)} \right| dk_1 dk_k.$ "

with: --
$$\int_{D^*} \frac{dp(|\beta - \beta_0|)}{d\Omega} \sqrt{k_1} \left| \frac{\partial(\theta, \phi)}{\partial(k_1 k_2)} \right| dk_1 dk_2.$$
--

Column 13, line 63, replace: $\frac{\partial\phi}{\partial k_1}$, $\frac{\partial\phi}{\partial k_2}$ "BRDF = "

with: --BRDF = --

Column 15, line 3, replace: " " with: --,--

Column 15, lines 32-33,  
replace: "$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha$"

UNITED STATES PATENT AND TRADEMARK OFFICE
CERTIFICATE OF CORRECTION

PATENT NO. : 7,119,903 B1  
APPLICATION NO. : 10/692704  
DATED : October 10, 2006  
INVENTOR(S) : Brian B. Jones Page 3 of 4

It is certified that error appears in the above-identified patent and that said Letters Patent is hereby corrected as shown below:

with: --$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha$--

Column 16, line 37, replace: $\frac{dp}{d\Omega} = \frac{1}{I_s l(r)r}\left(\frac{d\beta'}{dr}\right)\frac{dBRDF}{d\beta'}$ . "l(r)" with --$\ell(r)$--

Column 16, line 45, replace: "$\geq \cos\psi_{spec}\cos\phi + \sin\psi_{spec}\sin\phi$, and"

with: -- $\frac{dp}{d\Omega} = \frac{1}{I_s \ell(r)r}\left(\frac{d\beta'}{dr}\right)\frac{dBRDF}{d\beta'}$ . $\geq \cos\psi_{spec}\cos\phi + \sin\psi_{spec}\sin\phi$, and--

Column 16, line 50, replace: " $^2$   $^2$ "

with: -- $^2$ --

Column 17, line 19, delete: "; and"

Column 17, line 20, replace: "$p_{spec}^2 = \rho_0^2 - 2\rho_0 z_0 \cos\psi_0 \tan\theta_{spec} + z_0^2 \tan^2\theta_{spec}$"

with: --$p_{spec} = \rho_0 - 2\rho_0 z_0 \cos\psi_0 \tan\theta_{spec} + z_0 \tan^2\theta_{spec}$--

Column 17, line 22, add: --; and-- before "(c)".

Column 17, line 30, replace: "$\cos^{-1}(\sin\theta_1 \cos\phi_1 + \sin\theta_1 \sin\theta_2 \sin\phi_2 + \cos\theta_2) \leq \alpha$" $\frac{1}{P_i}\frac{1}{\Omega_i}\int_{\Omega i}\int_{Area s}\int_{\Omega d}\frac{d^2 P_i}{d\Omega_i dA}\frac{dp_d(\Omega_i,\Omega_d,A)}{d\Omega_d}d\Omega_i dA d\Omega_d$, $\sin\theta_2 \cos\phi_2 \sin\phi_1 \cos\theta_1$ $\frac{1}{P_i}\frac{1}{\Omega_i}\int_{\Omega i}\int_{Area}\int_{\Omega d}\frac{d^2 P_i}{d\Omega_i dA}\frac{dp_d(\Omega_i,\Omega_d,A)}{d\Omega_d}d\Omega_i dA d\Omega_d$, with: --$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha$--

IN THE CLAIMS:

Column 21, line 15, replace:

UNITED STATES PATENT AND TRADEMARK OFFICE
CERTIFICATE OF CORRECTION

PATENT NO. : 7,119,903 B1
APPLICATION NO. : 10/692704
DATED : October 10, 2006
INVENTOR(S) : Brian B. Jones It is certified that error appears in the above-identified patent and that said Letters Patent is hereby corrected as shown below:

"BRDF = "

$$\int_{D^*} \frac{dp(|\beta - \beta_0|)}{d\Omega} \sqrt{k_1} \left| \frac{\partial(\theta, \phi)}{\partial(k_1 k_2)} \right| dk_1 dk_2,$$

with: --BRDF = --

$$\int_{D^*} \frac{dp(|\beta - \beta_0|)}{d\Omega} \sqrt{k_1} \left| \frac{\partial(\theta, \phi)}{\partial(k_1, k_2)} \right| dk_1 dk_2,$$

Column 21, line 29, replace "P$_i$ is incident power of the electromagnetic radiation." with -- P$_i$ is the incident power of the electromagnetic radiation.--

Column 21, line 58, remove: "for" after "$|\beta\text{-}\beta_0| = \theta_i + \theta_d$".

Column 21, line 59, add: --for-- before "being".

Column 21, line 65, replace: "BRDF = "

with: --BRDF = --

Signed and Sealed this

Twenty-fifth Day of September, 2007

JON W. DUDAS
*Director of the United States Patent and Trademark Office*

UNITED STATES PATENT AND TRADEMARK OFFICE
CERTIFICATE OF CORRECTION

PATENT NO. : 7,119,903 B1
APPLICATION NO. : 10/692704
DATED : October 10, 2006
INVENTOR(S) : Brian B. Jones It is certified that error appears in the above-identified patent and that said Letters Patent is hereby corrected as shown below:

IN THE SPECIFICATION:

Column 6, Line 55: remove "(i.e.," after "integrand"

Column 10, line 20, replace: "$\rho_{spec}{}^2 = \rho_0{}^2 - 2\rho_0 z_0 \cos\psi_0 \tan\theta_{spec} + z_0{}^2 \tan^2 \theta_{spec}.$"
with: --$\rho_{spec}^2 = \rho_0^2 - 2\rho_0 z_0 \cos\psi_0 \tan\theta_{spec} + z_0^2 \tan^2 \theta_{spec}.$--

Column 10, line 22, replace: "$0 \leq r \leqq R$" with --$0 < r \leq R$--

Column 10, line 23, replace: "$0 < \phi \leqq 2\pi.$" with --$0 < \phi \leq 2\pi.$--

Column 10, line 49, replace: "$\rho^2 = \rho_{spec}{}^2 + r^2 + \rho_{spec} r \cos\psi_{spec} \cos\phi + \rho_{spec} \sin\psi_{spec} r \sin\phi.$"

with: --$\rho^2 = \rho_{spec}^2 + r^2 + \rho_{spec} r \cos\psi_{spec} \cos\phi + \rho_{spec} \sin\psi_{spec} r \sin\phi.$--

Column 10, line 52, replace: "$\rho \leqq R$" with --$\rho \leq R$--

Column 10, line 55, replace: "$\dfrac{R^2 - \rho_{spec}^2 - r^2}{\rho_{spec}^r} \geq \cos\psi_{spec} \cos\phi + \sin\psi_{spec} \sin\phi.$"

with: --$\dfrac{R^2 - \rho_{spec}^2 - r^2}{\rho_{spec} r} \geq \cos\psi_{spec} \cos\phi + \sin\psi_{spec} \sin\phi.$--

Column 10, line 59, delete equation: "$\geqq \cos\psi_{spec} \cos\phi + \sin\psi_{spec} \sin\phi.$"

Column 11, line 5, replace: "$\dfrac{R^2 - \rho_{spec}^2 - r^2}{\rho_{spec}^r} \geq \cos\psi_{spec} \cos\phi + \sin\psi_{spec} \sin\phi.$"

with: --$\dfrac{R^2 - \rho_{spec}^2 - r^2}{\rho_{spec} r} \geq \cos\psi_{spec} \cos\phi + \sin\psi_{spec} \sin\phi.$--

UNITED STATES PATENT AND TRADEMARK OFFICE
CERTIFICATE OF CORRECTION

PATENT NO. : 7,119,903 B1
APPLICATION NO. : 10/692704
DATED : October 10, 2006
INVENTOR(S) : Brian B. Jones It is certified that error appears in the above-identified patent and that said Letters Patent is hereby corrected as shown below:

Column 11, line 10, delete equation: "$\geq \cos\psi_{spec} \cos\phi + \sin\psi_{spec} \sin\phi.$"

Column 12, line 7, replace: "$\beta'^2 = \dfrac{z_0^2}{z_0^2 + r^2} - \dfrac{2z_0 \sin\theta_0}{\sqrt{z_0^2 + r^2}} + \sin^2\theta_0$"

with: -- $\beta'^2 = \dfrac{z_0^2}{z_0^2 + r^2} - \dfrac{2z_0 \sin\theta_0}{\sqrt{z_0^2 + r^2}} + \sin^2\theta_0$ --

Column 12, line 20, replace:

"$\dfrac{d\beta'}{dr} = \left( \dfrac{z_0^2}{z_0^2 + r^2} - \dfrac{2_{z_0} \sin\theta_0}{\sqrt{r^2 + z_0^2}} + \sin^2\theta_0 \right)^{-\frac{1}{2}} \left( \dfrac{z_0^2}{(z_0^2 + r^2)} - \dfrac{z_0 r \sin\theta_0}{(z_0^2 + r^2)^{(3/2)}} \right)$"

with: -- $\dfrac{d\beta'}{dr} = \left( \dfrac{z_0^2}{z_0^2 + r^2} - \dfrac{2_{z_0} \sin\theta_0}{\sqrt{r^2 + z_0^2}} + \sin^2\theta_0 \right)^{-\frac{1}{2}} \left( \dfrac{z_0^2}{(z_0^2 + r^2)} - \dfrac{z_0 r \sin\theta_0}{(z_0^2 + r^2)^{(3/2)}} \right)$ --

Column 12, line 37, replace: "$\dfrac{dp}{d\Omega} = \dfrac{1}{I_s l(r) r} \left( \dfrac{d\beta'}{dr} \right) \dfrac{dBRDF}{d\beta'} \cdot$"

with: -- $\dfrac{dp}{d\Omega} = \dfrac{1}{I_s \ell(r) r} \left( \dfrac{d\beta'}{dr} \right) \dfrac{dBRDF}{d\beta'} \cdot$ --

Column 13, line 63, replace: "$BRDF = \int_{D^*} \dfrac{dp(|\beta - \beta_0|)}{d\Omega} \sqrt{k_1} \left| \dfrac{\partial(\theta,\phi)}{\partial(k_1 k_2)} \right| dk_1 dk_k \cdot$"

with: --$BRDF = \int_{D^*} \dfrac{dp(|\beta - \beta_0|)}{d\Omega} \sqrt{k_1} \left| \dfrac{\partial(\theta,\phi)}{\partial(k_1 k_2)} \right| dk_1 dk_2 \cdot$--

Column 15, line 3, replace: "$\dfrac{\partial \phi}{\partial k_1},$" with: -- $\dfrac{\partial \phi}{\partial k_2},$--

Column 15, lines 32-33,
replace: "$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha$"

with: --$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha$--

UNITED STATES PATENT AND TRADEMARK OFFICE
CERTIFICATE OF CORRECTION

PATENT NO. : 7,119,903 B1
APPLICATION NO. : 10/692704
DATED : October 10, 2006
INVENTOR(S) : Brian B. Jones It is certified that error appears in the above-identified patent and that said Letters Patent is hereby corrected as shown below:

Column 16, line 37, replace: "l(r)" with --$\ell(r)$--

Column 16, line 45, replace: "$\geq \cos\psi_{spec} \cos\phi + \sin\psi_{spec} \sin\phi$, and"
with: --$\geq \cos\psi_{spec} \cos\phi + \sin\psi_{spec} \sin\phi$, and--

Column 16, line 50, replace: "$\dfrac{dp}{d\Omega} = \dfrac{1}{I_s l(r) r}\left(\dfrac{d\beta'}{dr}\right)\dfrac{dBRDF}{d\beta'} \cdot$"

with: --$\dfrac{dp}{d\Omega} = \dfrac{1}{I_s \ell(r) r}\left(\dfrac{d\beta'}{dr}\right)\dfrac{dBRDF}{d\beta'} \cdot$ --

Column 17, line 19, delete: "; and"

Column 17, line 20, replace: "$\rho_{spec}^2 = \rho_0^2 - 2\rho_0 z_0 \cos\psi_0 \tan\theta_{spec} + z_0^2 \tan^2 \theta_{spec}$"
with: --$\rho_{spec}^2 = \rho_0^2 - 2\rho_0 z_0 \cos\psi_0 \tan\theta_{spec} + z_0^2 \tan^2 \theta_{spec}$--

Column 17, line 22, add: --; and-- before "(c)".

Column 17, line 30,
replace: "$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha$"
with: --$\cos^{-1}(\sin\theta_1 \cos\phi_1 \sin\theta_2 \cos\phi_2 + \sin\theta_1 \sin\phi_1 \sin\theta_2 \sin\phi_2 + \cos\theta_1 \cos\theta_2) \leq \alpha$--

IN THE CLAIMS:

Column 21, line 15, replace:
"$BRDF = \dfrac{1}{P_i}\dfrac{1}{\Omega_i}\int_{\Omega i}\int_{Area\ s}\int_{\Omega d}\dfrac{d^2 P_i}{d\Omega_i dA}\dfrac{dp_d(\Omega_i, \Omega_d, A)}{d\Omega_d} d\Omega_i dA d\Omega_d$,"

with: --$BRDF = \dfrac{1}{P_i}\dfrac{1}{\Omega_i}\int_{\Omega i}\int_{Area}\int_{\Omega d}\dfrac{d^2 P_i}{d\Omega_i dA}\dfrac{dp_d(\Omega_i, \Omega_d, A)}{d\Omega_d} d\Omega_i dA d\Omega_d$, --

Column 21, line 29, replace "$P_i$ is incident power of the electromagnetic radiation."
with -- $P_i$ is the incident power of the electromagnetic radiation.--

UNITED STATES PATENT AND TRADEMARK OFFICE
CERTIFICATE OF CORRECTION

PATENT NO.       : 7,119,903 B1
APPLICATION NO.  : 10/692704
DATED            : October 10, 2006
INVENTOR(S)      : Brian B. Jones It is certified that error appears in the above-identified patent and that said Letters Patent is hereby corrected as shown below:

Column 21, line 58, remove: "for" after "$|\beta - \beta_0| = \theta_i + \theta_d$".

Column 21, line 59, add: --for-- before "being".

Column 21, line 65, replace: "$\text{BRDF} = \int_{D^*} \frac{dp(|\beta - \beta_0|)}{d\Omega} \sqrt{k_1} \left| \frac{\partial(\theta, \phi)}{\partial(k_1 k_2)} \right| dk_1 dk_2 ,$"

with: --$\text{BRDF} = \int_{D^*} \frac{dp(|\beta - \beta_0|)}{d\Omega} \sqrt{k_1} \left| \frac{\partial(\theta, \phi)}{\partial(k_1, k_2)} \right| dk_1 dk_2 ,$ --

This certificate supersedes Certificate of Correction issued September 25, 2007.

Signed and Sealed this

Twentieth Day of November, 2007

JON W. DUDAS
*Director of the United States Patent and Trademark Office*